(12) United States Patent
Ganeshalingam et al.

(10) Patent No.: US 8,412,462 B1
(45) Date of Patent: Apr. 2, 2013

(54) METHODS AND SYSTEMS FOR PROCESSING GENOMIC DATA

(75) Inventors: Lawrence Ganeshalingam, Dublin, CA (US); Patrick Nikita Allen, Scotts Valley, CA (US)

(73) Assignee: Annai Systems, Inc., Los Gatos, CA (US)

( * ) Notice: Subject to any disclaimer, the term of this patent is extended or adjusted under 35 U.S.C. 154(b) by 55 days.

(21) Appl. No.: 12/837,452

(22) Filed: Jul. 15, 2010

Related U.S. Application Data

(60) Provisional application No. 61/358,854, filed on Jun. 25, 2010.

(51) Int. Cl.
*G06F 19/00* (2011.01)
*G06F 19/10* (2011.01)

(52) U.S. Cl. ........................................................ 702/19

(58) Field of Classification Search ........................ None
See application file for complete search history.

(56) References Cited

U.S. PATENT DOCUMENTS

| | | | |
|---|---|---|---|
| 6,119,120 A | 9/2000 | Miller | |
| 7,158,892 B2 | 1/2007 | Robson et al. | |
| 7,820,378 B2 | 10/2010 | Van den Boom et al. | |
| 2003/0039362 A1 | 2/2003 | Califano et al. | |
| 2003/0055824 A1 | 3/2003 | Califano et al. | |
| 2003/0224419 A1 | 12/2003 | Corcoran et al. | |
| 2004/0005558 A1 | 1/2004 | Anderson et al. | |
| 2004/0006433 A1 | 1/2004 | Robson et al. | |
| 2005/0053968 A1 | 3/2005 | Bharadwaj et al. | |
| 2005/0267693 A1* | 12/2005 | Allard et al. | 702/20 |
| 2007/0190534 A1 | 8/2007 | Birch-Machin et al. | |
| 2007/0271604 A1 | 11/2007 | Webster et al. | |
| 2008/0077607 A1 | 3/2008 | Gatawood et al. | |
| 2010/0169313 A1 | 7/2010 | Kenedy et al. | |
| 2010/0169338 A1 | 7/2010 | Kenedy et al. | |
| 2010/0169340 A1 | 7/2010 | Kenedy et al. | |

FOREIGN PATENT DOCUMENTS

KR 1020070115964 A 12/2007

OTHER PUBLICATIONS

U.S. Appl. No. 12/828,234, filed Jun. 30, 2010.
U.S. Appl. No. 12/828,234 Non-Final Rejection mailed May 22, 2012.
PCT/US011/050078 International Search Report mailed Mar. 21, 2012.

* cited by examiner

*Primary Examiner* — Lori A Clow
(74) *Attorney, Agent, or Firm* — Cooley LLP

(57) ABSTRACT

A computer implemented method may be used to receive a sequence of binary codes representative of a biopolymeric data sequence and process the sequence of binary codes using instructions that are at least implicitly defined relative to at least one controlled sequence and representative of a biological event affecting one or more aspects of a biopolymeric molecule. A machine readable medium may contain a set of such instructions. The machine readable medium may be part of a genomics data processing system.

67 Claims, 14 Drawing Sheets

| DNA/RNA Nucleotide Base | Binary Coding |
|---|---|
| A (Adenine) | 00 |
| C (Cytosine) | 01 |
| G (Guanine) | 10 |
| T (Thymine) (Uracil in RNA) | 11 |

*FIG. 1*
Example Binary Encoding of Nucleotide Bases

Example Encoding of DNA Sequences Using Coding of FIG. 1 in Memory

300

| BIOLOGICAL EVENT | DESCRIPTION | INSTRUCTION FORMAT | COMMENTS |
|---|---|---|---|
| Transition | Replace G <-> A or C <-> T | TNST dest | Destination is the sequence entry transition result |
| Transversion | Replace G/A <-> C/T | TNSV src, dest | Source is converted to destination |
| Transversion (dest. only) | Replace G/A <-> C/T | TNSV dest | Destination is the sequence entry transversion result |
| Silent Mutation | Single base mutation that DOES NOT change amino acid sequence | SMUT src, dest | Source is converted to destination |
| Mis-sense | Single base mutation that DOES change the amino acid sequence | MISS src, dest | Source is converted to destination |
| Non-sense | Nucleotide substitution that creates one of three stop codons, producing a truncated protein | NONS src, dest | Source is converted to destination |
| Deletion | A nucleotide base has been removed from the sequence | DET src | The source is missing from the nucleotide sequence |
| Deletion Short (no operand) | Same as deletion except nucleotide base is not specified | DETS | Nucleotide base removed from sequence |
| Excision | A nucleotide sequence is removed, e.g., an integrated viral sequence | EXC len, Reg/Mem | Nucleotide sequence of length len deleted, deleted sequence is in location Reg/Mem (Reg/Mem is optional) |
| Insertion Short | Single insertion of nucleotide base | INSTS dst | The dst value is inserted into the nucleotide sequence |
| Insertion Long | Insertion of a sequence | INSTS len Reg/Mem | A nucleotide sequence of length len is inserted. The contents are in Reg/Mem location |
| Conjugation | Insertion of a bacterial sequence into the genome | CONJ len Reg/Mem | A bacterial sequence of length len is inserted. The content are in Reg/Mem location |
| Crossover | Rearrangement at the chromosomal level | CROSS len, addr | A sequence of length len is stored at address addr. Addr can be absolute or relative. With negative addressing value can be negative or positive |
| Jump Absolute | A sequence of pointers is updated by the jump absolute instruction | JMA addr | Move position pointer to the value of absolute address (A_addr) |
| Jump Relative | A sequence of pointers is updated by the jump relative address | JMPR addr | Move position pointer by adding relative address. Relative address may be positive or negative |
| Jump Fixed | Sequence pointer updated by fixed amount | JMPF Reg/Mem | Move position pointer by adding address specified by Reg/Mem location. Address may be positive or negative |

*FIG. 3*
*Example Instruction Set*

*Example Sequence Comparison*

Example Insertion Event

Example of Chromosomal Rearrangement
Event (Translocation)

Example of Alternate Splicing of mRNA

```
                        SEQUENCE LISTING

<160> NUMBER OF SEQ ID NOS: 24

<210> SEQ ID NO 1
<211> LENGTH: 30
<212> TYPE: DNA
<213> ORGANISM: Unknown
<220> FEATURE:
<223> OTHER INFORMATION: Exemplary nucleotide sequence

<400> SEQUENCE: 1
ccggtccagg ggacgcgacc aaaaagccca                                  30

<210> SEQ ID NO 2
<211> LENGTH: 30
<212> TYPE: DNA
<213> ORGANISM: Unknown
<220> FEATURE:
<223> OTHER INFORMATION: SEQ ID NO.:1 as represented by the following
      instruction set, denoted as Instructions 1, based on the
      instructions as defined in Table 300 of FIG. 3

<400> SEQUENCE: 2
ccagtccagg aaaaacgacg cgaccgccca                                  30

<210> SEQ ID NO 3
<211> LENGTH: 20
<212> TYPE: DNA
<213> ORGANISM: Unknown
<220> FEATURE:
<223> OTHER INFORMATION: Exemplary DNA sequence

<400> SEQUENCE: 3
acgccgtaac gggtaattca                                             20

<210> SEQ ID NO 4
<211> LENGTH: 20
<212> TYPE: DNA
<213> ORGANISM: Unknown
<220> FEATURE:
<223> OTHER INFORMATION: Exemplary DNA sequence

<400> SEQUENCE: 4
aagccgtaac gggtaattcg                                             20

<210> SEQ ID NO 5
<211> LENGTH: 20
<212> TYPE: DNA
<213> ORGANISM: Unknown
<220> FEATURE:
<223> OTHER INFORMATION: Exemplary DNA sequence

<400> SEQUENCE: 5
acgacgtaac gggtaattcg                                             20

<210> SEQ ID NO 6
<211> LENGTH: 20
<212> TYPE: DNA
<213> ORGANISM: Unknown
<220> FEATURE:
```

-continued

<223> OTHER INFORMATION: Exemplary DNA sequence

<400> SEQUENCE: 6
acgacgtatc gggtaattca 20

<210> SEQ ID NO 7
<211> LENGTH: 20
<212> TYPE: DNA
<213> ORGANISM: Unknown
<220> FEATURE:
<223> OTHER INFORMATION: Exemplary DNA sequence

<400> SEQUENCE: 7
acgacgtatc gggtaataca 20

<210> SEQ ID NO 8
<211> LENGTH: 20
<212> TYPE: DNA
<213> ORGANISM: Unknown
<220> FEATURE:
<223> OTHER INFORMATION: Exemplary DNA sequence

<400> SEQUENCE: 8
acgacgtaac gggtaattca 20

<210> SEQ ID NO 9
<211> LENGTH: 30
<212> TYPE: DNA
<213> ORGANISM: Unknown
<220> FEATURE:
<223> OTHER INFORMATION: Exemplary DNA sequence

<400> SEQUENCE: 9
gggggggggg gggggggggg gggggggggg 30

<210> SEQ ID NO 10
<211> LENGTH: 30
<212> TYPE: DNA
<213> ORGANISM: Unknown
<220> FEATURE:
<223> OTHER INFORMATION: Exemplary DNA sequence

<400> SEQUENCE: 10
gggggggggg ggggtggggg gggggggggg 30

<210> SEQ ID NO 11
<211> LENGTH: 3000
<212> TYPE: DNA
<213> ORGANISM: Unknown
<220> FEATURE:
<223> OTHER INFORMATION: Exemplary DNA sequence
<220> FEATURE:
<221> NAME/KEY: misc_feature
<222> LOCATION: (21)..(2990)
<223> OTHER INFORMATION: May be a known sequence that belongs to a
particular strain of the influenza virus

<400> SEQUENCE: 11
gggggggggg ggggtggggg nnnnnnnnnn nnnnnnnnnn nnnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnn nnnnnnnnnn nnnnnnnnnn nnnnnnnnnn nnnnnnnnnn 360

| | |
|---|---|
| nnnnnnnnnn nnnnnnnnnn nnnnnnnnnn nnnnnnnnnn nnnnnnnnnn nnnnnnnnnn | 420 |
| nnnnnnnnnn nnnnnnnnnn nnnnnnnnnn nnnnnnnnnn nnnnnnnnnn nnnnnnnnnn | 480 |
| nnnnnnnnnn nnnnnnnnnn nnnnnnnnnn nnnnnnnnnn nnnnnnnnnn nnnnnnnnnn | 540 |
| nnnnnnnnnn nnnnnnnnnn nnnnnnnnnn nnnnnnnnnn nnnnnnnnnn nnnnnnnnnn | 600 |
| nnnnnnnnnn nnnnnnnnnn nnnnnnnnnn nnnnnnnnnn nnnnnnnnnn nnnnnnnnnn | 660 |
| nnnnnnnnnn nnnnnnnnnn nnnnnnnnnn nnnnnnnnnn nnnnnnnnnn nnnnnnnnnn | 720 |
| nnnnnnnnnn nnnnnnnnnn nnnnnnnnnn nnnnnnnnnn nnnnnnnnnn nnnnnnnnnn | 780 |
| nnnnnnnnnn nnnnnnnnnn nnnnnnnnnn nnnnnnnnnn nnnnnnnnnn nnnnnnnnnn | 840 |
| nnnnnnnnnn nnnnnnnnnn nnnnnnnnnn nnnnnnnnnn nnnnnnnnnn nnnnnnnnnn | 900 |
| nnnnnnnnnn nnnnnnnnnn nnnnnnnnnn nnnnnnnnnn nnnnnnnnnn nnnnnnnnnn | 960 |
| nnnnnnnnnn nnnnnnnnnn nnnnnnnnnn nnnnnnnnnn nnnnnnnnnn nnnnnnnnnn | 1020 |
| nnnnnnnnnn nnnnnnnnnn nnnnnnnnnn nnnnnnnnnn nnnnnnnnnn nnnnnnnnnn | 1080 |
| nnnnnnnnnn nnnnnnnnnn nnnnnnnnnn nnnnnnnnnn nnnnnnnnnn nnnnnnnnnn | 1140 |
| nnnnnnnnnn nnnnnnnnnn nnnnnnnnnn nnnnnnnnnn nnnnnnnnnn nnnnnnnnnn | 1200 |
| nnnnnnnnnn nnnnnnnnnn nnnnnnnnnn nnnnnnnnnn nnnnnnnnnn nnnnnnnnnn | 1260 |
| nnnnnnnnnn nnnnnnnnnn nnnnnnnnnn nnnnnnnnnn nnnnnnnnnn nnnnnnnnnn | 1320 |
| nnnnnnnnnn nnnnnnnnnn nnnnnnnnnn nnnnnnnnnn nnnnnnnnnn nnnnnnnnnn | 1380 |
| nnnnnnnnnn nnnnnnnnnn nnnnnnnnnn nnnnnnnnnn nnnnnnnnnn nnnnnnnnnn | 1440 |
| nnnnnnnnnn nnnnnnnnnn nnnnnnnnnn nnnnnnnnnn nnnnnnnnnn nnnnnnnnnn | 1500 |
| nnnnnnnnnn nnnnnnnnnn nnnnnnnnnn nnnnnnnnnn nnnnnnnnnn nnnnnnnnnn | 1560 |
| nnnnnnnnnn nnnnnnnnnn nnnnnnnnnn nnnnnnnnnn nnnnnnnnnn nnnnnnnnnn | 1620 |
| nnnnnnnnnn nnnnnnnnnn nnnnnnnnnn nnnnnnnnnn nnnnnnnnnn nnnnnnnnnn | 1680 |
| nnnnnnnnnn nnnnnnnnnn nnnnnnnnnn nnnnnnnnnn nnnnnnnnnn nnnnnnnnnn | 1740 |
| nnnnnnnnnn nnnnnnnnnn nnnnnnnnnn nnnnnnnnnn nnnnnnnnnn nnnnnnnnnn | 1800 |
| nnnnnnnnnn nnnnnnnnnn nnnnnnnnnn nnnnnnnnnn nnnnnnnnnn nnnnnnnnnn | 1860 |
| nnnnnnnnnn nnnnnnnnnn nnnnnnnnnn nnnnnnnnnn nnnnnnnnnn nnnnnnnnnn | 1920 |
| nnnnnnnnnn nnnnnnnnnn nnnnnnnnnn nnnnnnnnnn nnnnnnnnnn nnnnnnnnnn | 1980 |
| nnnnnnnnnn nnnnnnnnnn nnnnnnnnnn nnnnnnnnnn nnnnnnnnnn nnnnnnnnnn | 2040 |
| nnnnnnnnnn nnnnnnnnnn nnnnnnnnnn nnnnnnnnnn nnnnnnnnnn nnnnnnnnnn | 2100 |
| nnnnnnnnnn nnnnnnnnnn nnnnnnnnnn nnnnnnnnnn nnnnnnnnnn nnnnnnnnnn | 2160 |
| nnnnnnnnnn nnnnnnnnnn nnnnnnnnnn nnnnnnnnnn nnnnnnnnnn nnnnnnnnnn | 2220 |
| nnnnnnnnnn nnnnnnnnnn nnnnnnnnnn nnnnnnnnnn nnnnnnnnnn nnnnnnnnnn | 2280 |
| nnnnnnnnnn nnnnnnnnnn nnnnnnnnnn nnnnnnnnnn nnnnnnnnnn nnnnnnnnnn | 2340 |
| nnnnnnnnnn nnnnnnnnnn nnnnnnnnnn nnnnnnnnnn nnnnnnnnnn nnnnnnnnnn | 2400 |
| nnnnnnnnnn nnnnnnnnnn nnnnnnnnnn nnnnnnnnnn nnnnnnnnnn nnnnnnnnnn | 2460 |
| nnnnnnnnnn nnnnnnnnnn nnnnnnnnnn nnnnnnnnnn nnnnnnnnnn nnnnnnnnnn | 2520 |
| nnnnnnnnnn nnnnnnnnnn nnnnnnnnnn nnnnnnnnnn nnnnnnnnnn nnnnnnnnnn | 2580 |
| nnnnnnnnnn nnnnnnnnnn nnnnnnnnnn nnnnnnnnnn nnnnnnnnnn nnnnnnnnnn | 2640 |
| nnnnnnnnnn nnnnnnnnnn nnnnnnnnnn nnnnnnnnnn nnnnnnnnnn nnnnnnnnnn | 2700 |
| nnnnnnnnnn nnnnnnnnnn nnnnnnnnnn nnnnnnnnnn nnnnnnnnnn nnnnnnnnnn | 2760 |

```
nnnnnnnnnn nnnnnnnnnn nnnnnnnnnn nnnnnnnnnn nnnnnnnnnn nnnnnnnnnn      2820
nnnnnnnnnn nnnnnnnnnn nnnnnnnnnn nnnnnnnnnn nnnnnnnnnn nnnnnnnnnn      2880
nnnnnnnnnn nnnnnnnnnn nnnnnnnnnn nnnnnnnnnn nnnnnnnnnn nnnnnnnnnn      2940
nnnnnnnnnn nnnnnnnnnn nnnnnnnnnn nnnnnnnnnn nnnnnnnnnn gggggggggg      3000

<210> SEQ ID NO 12
<211> LENGTH: 612
<212> TYPE: DNA
<213> ORGANISM: Unknown
<220> FEATURE:
<223> OTHER INFORMATION: Exemplary CGG tandem repeats in the FMR1 gene

<400> SEQUENCE: 12
cggcggcggc ggcggcggcg gcggcggcgg cggcggcggc ggcggcggcg gcggcggcgg       60
cggcggcggc ggcggcggcg gcggcggcgg cggcggcggc ggcggcggcg gcggcggcgg      120
cggcggcggc ggcggcggcg gcggcggcgg cggcggcggc ggcggcggcg gcggcggcgg      180
cggcggcggc ggcggcggcg gcggcggcgg cggcggcggc ggcggcggcg gcggcggcgg      240
cggcggcggc ggcggcggcg gcggcggcgg cggcggcggc ggcggcggcg gcggcggcgg      300
cggcggcggc ggcggcggcg gcggcggcgg cggcggcggc ggcggcggcg gcggcggcgg      360
cggcggcggc ggcggcggcg gcggcggcgg cggcggcggc ggcggcggcg gcggcggcgg      420
cggcggcggc ggcggcggcg gcggcggcgg cggcggcggc ggcggcggcg gcggcggcgg      480
cggcggcggc ggcggcggcg gcggcggcgg cggcggcggc ggcggcggcg gcggcggcgg      540
cggcggcggc ggcggcggcg gcggcggcgg cggcggcggc ggcggcggcg gcggcggcgg      600
cggcggcggc gg                                                         612

<210> SEQ ID NO 13
<211> LENGTH: 15
<212> TYPE: DNA
<213> ORGANISM: Unknown
<220> FEATURE:
<223> OTHER INFORMATION: Exemplary DNA sequence

<400> SEQUENCE: 13
acgtagggca ttgca                                                       15

<210> SEQ ID NO 14
<211> LENGTH: 14
<212> TYPE: DNA
<213> ORGANISM: Unknown
<220> FEATURE:
<223> OTHER INFORMATION: Exemplary DNA sequence

<400> SEQUENCE: 14
acctaggcat tgca                                                        14

<210> SEQ ID NO 15
<211> LENGTH: 39
<212> TYPE: DNA
<213> ORGANISM: Unknown
<220> FEATURE:
<223> OTHER INFORMATION: Exemplary DNA sequence

<400> SEQUENCE: 15
gacttacggc aaatgtgtgc caaagaggcg gcacataag                             39

<210> SEQ ID NO 16
<211> LENGTH: 39
```

```
<212> TYPE: DNA
<213> ORGANISM: Unknown
<220> FEATURE:
<223> OTHER INFORMATION: Exemplary DNA sequence

<400> SEQUENCE: 16
gattttaaaa aggcagttgg tgccttttct gtaacttat                              39

<210> SEQ ID NO 17
<211> LENGTH: 39
<212> TYPE: DNA
<213> ORGANISM: Unknown
<220> FEATURE:
<223> OTHER INFORMATION: Exemplary DNA sequence

<400> SEQUENCE: 17
gatccagaaa attatcagct tgtcattttg tccatcaat                              39

<210> SEQ ID NO 18
<211> LENGTH: 39
<212> TYPE: DNA
<213> ORGANISM: Unknown
<220> FEATURE:
<223> OTHER INFORMATION: Exemplary DNA sequence

<400> SEQUENCE: 18
gaagtcacct caaagcgagc acatatgctg attgacatc                              39

<210> SEQ ID NO 19
<211> LENGTH: 39
<212> TYPE: DNA
<213> ORGANISM: Unknown
<220> FEATURE:
<223> OTHER INFORMATION: Exemplary DAN sequence

<400> SEQUENCE: 19
cactttcgga gtctgcgcac taagttgtct ctgataatg                              39

<210> SEQ ID NO 20
<211> LENGTH: 34
<212> TYPE: DNA
<213> ORGANISM: Unknown
<220> FEATURE:
<223> OTHER INFORMATION: Exemplary DNA sequence

<400> SEQUENCE: 20
acgggagcat catcatcctt acttacttcc aagg                                   34

<210> SEQ ID NO 21
<211> LENGTH: 32
<212> TYPE: DNA
<213> ORGANISM: Unknown
<220> FEATURE:
<223> OTHER INFORMATION: Exemplary DNA sequence

<400> SEQUENCE: 21
acgggcgcat catcacctta cttacttcca ag                                     32

<210> SEQ ID NO 22
<211> LENGTH: 33
<212> TYPE: DNA
<213> ORGANISM: Unknown
<220> FEATURE:
<223> OTHER INFORMATION: Exemplary DNA sequence

<400> SEQUENCE: 22
acgggcgcat catcatcctt acttacttcc aag                                    33
```

```
-continued

<210> SEQ ID NO 23
<211> LENGTH: 35
<212> TYPE: DNA
<213> ORGANISM: Unknown
<220> FEATURE:
<223> OTHER INFORMATION: Exemplary DNA sequence

<400> SEQUENCE: 23
acgggcgcat catcatcctt acccttactt ccaag                              35

<210> SEQ ID NO 24
<211> LENGTH: 33
<212> TYPE: DNA
<213> ORGANISM: Unknown
<220> FEATURE:
<223> OTHER INFORMATION: Exemplary DNA sequence

<400> SEQUENCE: 24
acgggcgcat catcatcctt cttccaagac tta                                33
```

METHODS AND SYSTEMS FOR PROCESSING GENOMIC DATA

CROSS-REFERENCE TO RELATED APPLICATIONS

This application claims priority under 35 U.S.C. §119(e) to U.S. Provisional Patent Application Ser. No. 61/358,854, entitled METHODS AND SYSTEMS FOR PROCESSING GENOMICS DATA, filed on Jun. 25, 2010. This application is also related to U.S. Utility patent application Ser. No. 12/828,234, entitled METHODS AND SYSTEMS FOR PROCESSING GENOMIC DATA, filed on Jun. 30, 2010. The content of each of these applications is incorporated by reference herein in its entirety for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ANNA_002_02US_SeqList_ST25.txt, date recorded: Oct. 20, 2010, file size 10 kilobytes).

FIELD

This application is directed generally to the processing of genomic and other biopolymeric information. More particularly, but not exclusively, the application relates to a novel instruction set architecture for processing biopolymeric information, such as biological sequence data, as well as to systems and methods adapted to utilize the novel instruction set architecture.

BACKGROUND

Deoxyribonucleic acid ("DNA") sequencing is the process of determining the ordering of nucleotide bases (adenine (A), guanine (G), cytosine (C) and thymine (T)) in molecular DNA. Knowledge of DNA sequences is invaluable in basic biological research as well as in numerous applied fields such as, but not limited to, medicine, health, agriculture, livestock, population genetics, social networking, biotechnology, forensic science, security, and other areas of biology and life sciences.

Sequencing has been done since the 1970s, when academic researchers began using laborious methods based on two-dimensional chromatography. Due to the initial difficulties in sequencing in the early 1970s, the cost and speed could be measured in scientist years per nucleotide base as researchers set out to sequence the first restriction endonuclease site containing just a handful of bases.

Thirty years later, the entire 3.2 billion bases of the human genome have been sequenced, with a first complete draft of the human genome done at a cost of about three billion dollars. Since then sequencing costs have rapidly decreased. Today, many expect the cost of sequencing the human genome to be in the hundreds of dollars or less in the near future, with the results available in minutes, much like a routine blood test.

As the cost of sequencing the human genome continues to decrease, the number of individuals having their DNA sequenced for medical, as well as other purposes, will likely explode. Moreover, sequencing of other organisms will likely also increase for research purposes as well as disease analysis. Because of the large size of DNA sequences for many organisms, including humans, this explosion will lead to problems with DNA sequence data storage, processing, transmission, networking and analysis. Accordingly, there is a need in the art to address these problems as well as others.

SUMMARY

This application is directed generally to the processing of genomic and other biopolymeric information. More particularly, but not exclusively, the application relates to a novel instruction set architecture for processing biopolymeric information, such as biological sequence data, as well as to systems and methods adapted to utilize the novel instruction set architecture.

In one aspect, the disclosure relates to an article of manufacture in a system for processing biopolymeric information, where the article of manufacture comprises a machine readable medium containing an instruction set architecture including a plurality of instructions for execution by a processor, each of the plurality of instructions being at least implicitly defined relative to at least one controlled sequence, and representative of a biological, chemical, physical or other event affecting one or more aspects of a biopolymeric molecule.

In another aspect, the disclosure relates to an apparatus for processing biopolymeric information, the apparatus comprising a program memory for storing a plurality of instructions representative of a corresponding plurality of biological events affecting aspects of a biopolymeric molecule wherein each of the plurality of instructions is at least implicitly defined relative to a controlled sequence and a processing engine for executing ones of the plurality of instructions.

In another aspect, the disclosure relates to an apparatus for processing biopolymeric information, the apparatus comprising means for storing a plurality of instructions representative of a corresponding plurality of biological events affecting aspects of a biopolymeric molecule, wherein each of the plurality of instructions is at least implicitly defined relative to a controlled sequence, and means for executing ones of the plurality of instructions.

In another aspect, the disclosure relates to a computer-implemented method for processing biopolymeric information, the method comprising receiving a sequence of binary codes representative of a biopolymeric data sequence and processing the sequence of binary codes using a plurality of instructions, each of the plurality of instructions being at least implicitly defined relative to at least one controlled sequence and representative of a biological event affecting one or more aspects of a biopolymeric molecule.

In another aspect, the disclosure relates to a computer program product comprising a computer readable medium including codes for causing a computer to receive a sequence of binary codes representative of a biopolymeric data sequence and process the sequence of binary codes using a plurality of instructions, each of the plurality of instructions being at least implicitly defined relative to at least one controlled sequence and representative of a biological, chemical, physical, or other event affecting one or more aspects of a biopolymeric molecule.

In another aspect, the disclosure relates to an article of manufacture in a system for processing nucleic acid sequence information, the article of manufacture comprising a machine readable medium containing an instruction set architecture including a plurality of instructions for execution by a processor, wherein at least one of the plurality of instructions is useable to program a mutation event within a nucleic acid sequence.

In another aspect, the disclosure relates to an article of manufacture in a system for processing DNA sequence information, the article of manufacture comprising a machine readable medium containing an instruction set architecture including a plurality of instructions for execution by a processor wherein at least one of the plurality of instructions is useable to program a chromosome translocation event.

In another aspect, the disclosure relates to an article of manufacture in a system for processing nucleic acid sequence information, the article of manufacture comprising a machine readable medium containing an instruction set architecture including a plurality of instructions for execution by a processor wherein at least one of the plurality of instructions is useable to program a splicing event involving a nucleic acid sequence.

In another aspect, the disclosure relates to an article of manufacture in a system for processing nucleic acid sequence information, the article of manufacture comprising a machine readable medium containing an instruction set architecture including a plurality of instructions for execution by a processor, wherein at least one of the plurality of instructions is useable to determine the presence of a transposable element within a nucleic acid sequence.

In another aspect, the disclosure relates to a computer-implemented method for processing nucleic acid sequence information comprising receiving an input binary sequence containing information representing a nucleic acid sequence and identifying a segment of the input binary sequence corresponding to a transposable element.

In another aspect, the disclosure relates to a computer program product comprising a computer readable medium including codes for causing a computer to receive an input binary sequence containing information representing a nucleic acid sequence and identify a segment of the input binary sequence corresponding to a transposable element.

In another aspect, the disclosure relates to an article of manufacture in a system for processing nucleic acid sequence information, the article of manufacture comprising a machine readable medium containing an instruction set architecture including a plurality of instructions for execution by a processor, wherein at least one of the plurality of instructions is useable to discriminate between the insertion of a first nucleic acid sequence into a second nucleic acid sequence and a rearrangement of elements within the second nucleic acid sequence.

Additional aspects of the disclosure are described below in conjunction with the appended drawings.

BRIEF DESCRIPTION OF THE DRAWINGS

The present application may be more fully appreciated in connection with the following detailed description taken in conjunction with the accompanying drawings, wherein:

FIG. 1 illustrates details of an example binary coding scheme for base nucleotides in a DNA sequence;

FIG. 3 illustrates one embodiment of an instruction set for processing biological sequences;

DETAILED DESCRIPTION

Overview

Figure 2:
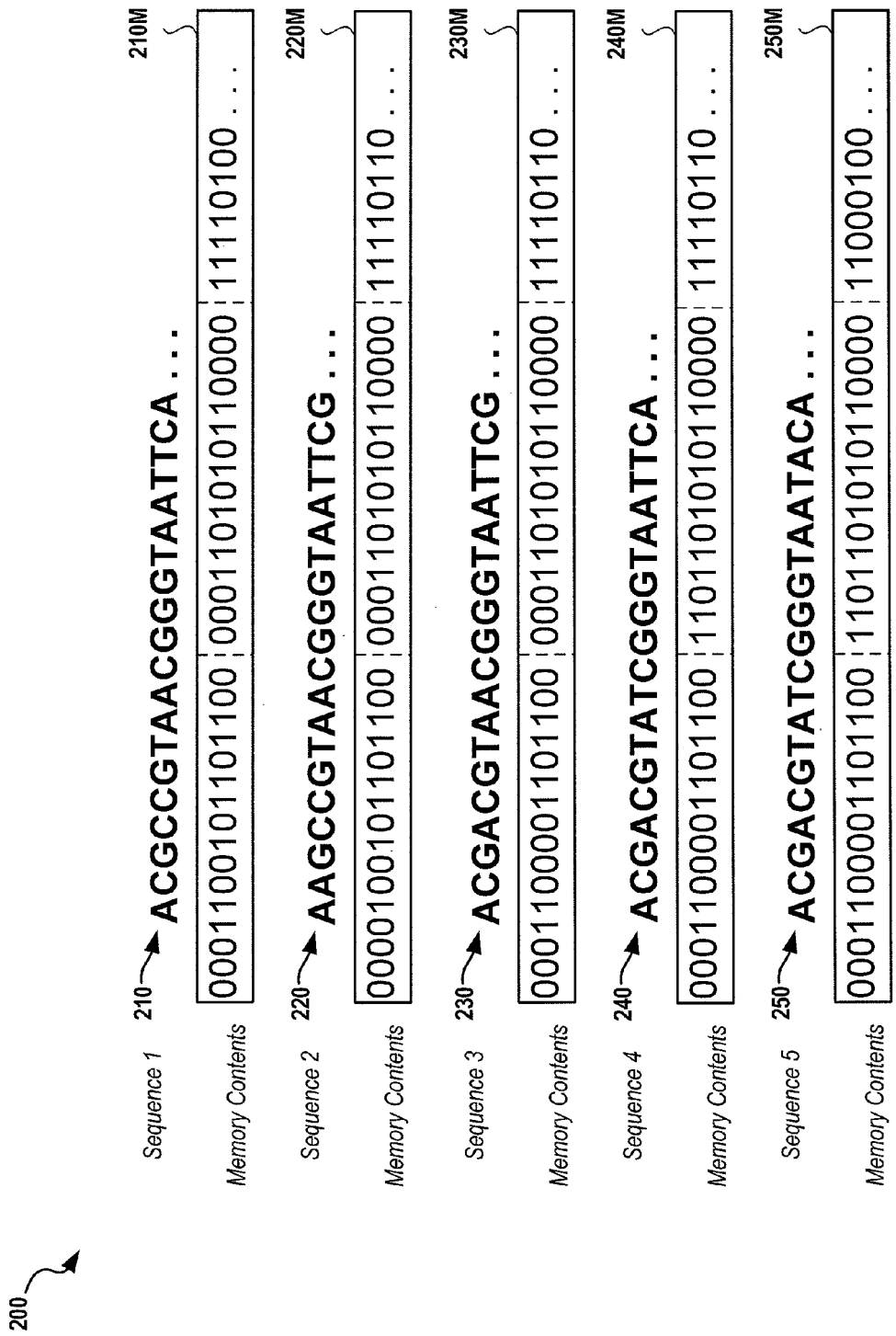
FIG. 2 illustrates an example of a set of binary encoded DNA sequences (SEQ ID NOS.: 3-7) stored in a memory using the binary coding of FIG. 1.

This disclosure relates generally to compressing, processing, storage, analysis, and transmission of biological sequences such as DNA sequences. More particularly, but not exclusively, the disclosure relates to instruction set architectures including instructions for processing biological sequences, along with associated biological sequence processing methods and apparatus configured to implement the instructions. In addition, a computer storage media may contain the instructions, and a sequence processing system may contain the storage media and a processing apparatus configured to implement the processing defined by the instructions. In addition, a computer data storage product may contain sequence data encoded using instruction-based encoding.

In one aspect, the disclosure relates to an article of manufacture in a system for processing biopolymeric information, where the article of manufacture comprises a machine readable medium containing an instruction set architecture including a plurality of instructions for execution by a processor, each of the plurality of instructions being at least implicitly defined relative to at least one controlled sequence, and representative of a biological event affecting one or more aspects of a biopolymeric molecule.

The plurality of instructions may include an opcode corresponding to the biological event and an operand relating to at least a portion of a monomer sequence of the biopolymeric molecule. The one or more aspects may include a monomer sequence of the biopolymeric molecule. The one or more aspects may include a structure of the biopolymeric molecule. The biopolymeric molecule may comprises a DNA molecule and the monomer sequence may comprise at least a portion of a nucleotide base sequence of the DNA molecule.

The biological event may comprise a transition and the operand may comprise at least a first nucleotide base. The operand may further comprise a second nucleotide base corresponding to a result of a transition of the first nucleotide base. The biological event may comprise a deletion. The biological event may comprise a transversion and the operand may comprise at least a first nucleotide base. The operand may further comprise a second nucleotide base corresponding to a result of a transversion of the first nucleotide base.

The biological event may comprise a silent mutation and the operand may comprise a first nucleotide base and a second nucleotide base. The biological event may comprise a mis-sense and the operand may comprise at least a first nucleotide base. The operand may further comprise a second nucleotide base corresponding to a result of a mis-sense of the first nucleotide base. The biological event may comprise a non-sense and the operand may comprise at least a first nucleotide base. The operand may further comprise a second nucleotide base corresponding to a result of a non-sense of the first nucleotide base. The biological event may comprise an excision and the operand may comprise a sequence length. The biological event may comprise a cross-over and the operand may comprise at least a sequence length.

The biological event represented by a first of the plurality of instructions may comprise a transition and the biological event represented by a second of the plurality of instructions may comprise a transversion. The biological event represented by a third of the plurality of instructions may comprise a mis-sense and the biological event represented by a fourth of the plurality of instructions may be a non-sense. The biological event represented by a fifth of the plurality of instructions may comprise a silent mutation and the biological event represented by a sixth of the plurality of instructions may comprise an excision.

The biopolymeric molecule may comprise an mRNA molecule. The biological event represented by one of the plurality of instructions may comprise a constitutive or alternate splice and the operand may identify at least one intron or exon.

One or more of the plurality of instructions may be used to create a delta representation of the nucleotide base sequence relative to the controlled sequence. The delta representation may be based at least in part upon modifications of nucleotide bases in the nucleotide base sequence relative to nucleotide bases of the controlled sequence. The modifications may include one of methylation, carboxylation, formylation, deamination, and other base modifications or analogs. The delta representation may be based at least in part upon one or more structural differences between the DNA molecule and a controlled molecular structure. The one or more structural differences may relate to DNA packaging. The one or more structural differences may relate to chromatin or heterochromatin structure.

One or more of the plurality of instructions may be configured so as to facilitate additional processing. The additional processing may relate to determination of a biological characteristic or property of an organism associated with the instructions. The determination may be based on or related to the biological event.

In another aspect, the disclosure relates to an apparatus for processing biopolymeric information, the apparatus comprising a program memory for storing a plurality of instructions representative of a corresponding plurality of biological events affecting aspects of a biopolymeric molecule wherein each of the plurality of instructions is at least implicitly defined relative to a controlled sequence and a processing engine for executing ones of the plurality of instructions.

One of the plurality of instructions may include an opcode corresponding to one of the plurality of biological events and an operand relating to at least a portion of a monomer sequence of the biopolymeric molecule. The aspects may include a monomer sequence of the biopolymeric molecule and a structure of the biopolymeric molecule. The biopolymeric molecule may comprise a DNA molecule.

The biological event may comprise a transition and the operand may comprise at least a first nucleotide base. The operand may further comprise a second nucleotide base corresponding to a result of a transition of the first nucleotide base. The biological event may comprise a deletion. The biological event may comprise a transversion and the operand may comprise at least a first nucleotide base. The operand may further comprise a second nucleotide base corresponding to a result of a transversion of the first nucleotide base.

The biological event may comprise a silent mutation and the operand may comprise a first nucleotide base and a second nucleotide base. The biological event may comprise a mis-sense and the operand may comprise at least a first nucleotide base. The operand may further comprise a second nucleotide base corresponding to a result of a mis-sense of the first nucleotide base.

The biological event may comprise a non-sense and the operand may comprise at least a first nucleotide base. The operand may further comprise a second nucleotide base corresponding to a result of a non-sense of the first nucleotide base. The biological event may comprise an excision and the operand may comprise a sequence length. The biological event may comprise a cross-over and the operand may comprise at least a sequence length.

The biological event represented by a first of the plurality of instructions may comprise a transition and the biological event represented by a second of the plurality of instructions may comprise a transversion. The biological event represented by a third of the plurality of instructions may comprise a mis-sense and the biological event represented by a fourth of the plurality of instructions may comprise a non-sense. The biological event represented by a fifth of the plurality of instructions may comprise a silent mutation and the biological event represented by a sixth of the plurality of instructions may comprise an excision.

The biopolymeric molecule may comprise an mRNA molecule. The biological event represented by one of the plurality of instructions may comprise a constitutive or alternate splice event and the operand may comprise at least one intron or exon.

The one or more of the plurality of instructions may be configured to generate a delta representation of a nucleotide base sequence of the DNA molecule relative to the controlled sequence. The delta representation may be based at least in part upon modifications of nucleotide bases in the nucleotide base sequence relative to nucleotide bases of the controlled sequence. The modifications may include one of methylation, carboxylation, formylation, deamination, and/or other base modification or analogs. The delta representation may be based at least in part upon one or more structural differences between the DNA molecule and a controlled molecular structure. The one or more structural differences may relate to DNA packaging. The one or more structural differences may relate to chromatin or heterochromatin structure.

In another aspect, the disclosure relates to an apparatus for processing biopolymeric information, the apparatus comprising means for storing a plurality of instructions representative of a corresponding plurality of biological events affecting aspects of a biopolymeric molecule, wherein each of the plurality of instructions is at least implicitly defined relative to a controlled sequence, and means for executing ones of the plurality of instructions.

The method may further include defining one or more macro instructions comprised of two or more instructions of the plurality of instructions and processing the sequence of binary codes using the one or more macro instructions.

The processing may include deriving a delta representation of the biopolymeric data sequence using a reference sequence. The biopolymeric data sequence may comprise a DNA sequence. The delta representation may be based at least upon differences between a nucleotide base sequence of the biopolymeric data sequence and a reference nucleotide base sequence of the reference sequence. The delta representation may be further based upon modifications of nucleotide bases in the nucleotide base sequence of the biopolymeric data sequence relative to nucleotide bases in the reference base sequence. One or more of the plurality of instructions may be used to represent a mutation in the biopolymeric data sequence.

In another aspect, the disclosure relates to a computer program product comprising a computer readable medium including codes for causing a computer to receive a sequence of binary codes representative of a biopolymeric data sequence and process the sequence of binary codes using a plurality of instructions, each of the plurality of instructions being at least implicitly defined relative to at least one controlled sequence and representative of a biological event affecting one or more aspects of a biopolymeric molecule.

In another aspect, the disclosure relates to an article of manufacture in a system for processing nucleic acid sequence information, the article of manufacture comprising a machine readable medium containing an instruction set architecture including a plurality of instructions for execution by a processor, wherein at least one of the plurality of instructions is useable to program a mutation event within a nucleic acid sequence.

In another aspect, the disclosure relates to an article of manufacture in a system for processing DNA sequence information, the article of manufacture comprising a machine readable medium containing an instruction set architecture including a plurality of instructions for execution by a processor wherein at least one of the plurality of instructions is useable to program a chromosome translocation event.

The one or more of the plurality of instructions may be at least implicitly defined relative to at least one controlled sequence.

In another aspect, the disclosure relates to an article of manufacture in a system for processing nucleic acid sequence information, the article of manufacture comprising a machine readable medium containing an instruction set architecture including a plurality of instructions for execution by a processor wherein at least one of the plurality of instructions is useable to program a splicing event involving a nucleic acid sequence.

One or more of the plurality of instructions may represent a first alternative splicing event involving the nucleic acid sequence. An additional one or more of the plurality of instructions may represent a second alternative splicing event involving the nucleic acid sequence. One or more of the plurality of instructions may be representative of at least one of disease association, gene activation, exon expression, exon inclusion and exon skipping associated with the splicing event. One or more of the plurality of instructions may be at least implicitly defined relative to at least one controlled sequence. One or more of the instructions may include a splice instruction having an operand identifying at least one splice donor site and at least one splice acceptor site. One or more instructions may include a splice instruction that specifies a sequence of jump operations.

In another aspect, the disclosure relates to an article of manufacture in a system for processing nucleic acid sequence information, the article of manufacture comprising a machine readable medium containing an instruction set architecture including a plurality of instructions for execution by a processor, wherein at least one of the plurality of instructions is useable to determine the presence of a transposable element within a nucleic acid sequence.

The transposable element may affect gene expression. The transposable element may affect gene regulation and/or expression. The transposable element may comprise a bacterial nucleic acid sequence. The transposable element may comprise a viral nucleic acid sequence.

In another aspect, the disclosure relates to a computer-implemented method for processing nucleic acid sequence information comprising receiving an input binary sequence containing information representing a nucleic acid sequence and identifying a segment of the input binary sequence corresponding to a transposable element.

In another aspect, the disclosure relates to a computer program product comprising a computer readable medium including codes for causing a computer to receive an input binary sequence containing information representing a nucleic acid sequence and identify a segment of the input binary sequence corresponding to a feature or a partial sequence of a transposable element.

In another aspect, the disclosure relates to an article of manufacture in a system for processing nucleic acid sequence information, the article of manufacture comprising a machine readable medium containing an instruction set architecture including a plurality of instructions for execution by a processor, wherein at least one of the plurality of instructions is useable to discriminate between the insertion of a first nucleic acid sequence into a second nucleic acid sequence and a rearrangement of elements within the second nucleic acid sequence.

The first nucleic acid sequence may comprise at least a portion of a DNA sequence of a microbial agent.

Various additional aspects of the present invention are described below. It should be apparent that the teachings herein may be embodied in a wide variety of forms and that any specific structure, function, or both being disclosed herein is merely representative and not intended to be limiting. Based on the teachings herein one skilled in the art should appreciate that an aspect disclosed herein may be implemented independently of any other aspects and that two or more of these aspects may be combined in various ways. For example, an apparatus or system may be implemented or a method may be practiced using any number of the aspects set forth herein. In addition, such an apparatus or system may be implemented or such a method may be practiced using other structure, functionality, or structure and functionality in addition to or other than one or more of the aspects set forth herein. Furthermore, an aspect may comprise at least one element of a claim.

While the embodiments described below are generally based on sequences of DNA, it will be apparent that embodiments of the present invention may equally be implemented for processing other biological sequences, such as RNA sequences, protein sequences, or other types of biological sequences. Accordingly, the present invention is not in any way limited in application to DNA sequences, but may rather be applied to a wide range of other biological sequences, as well as, in some applications, non-biological data sequences.

Genomic Sequencing

Genomic sequences are sequences of data describing genomic characteristics of a particular organism. The term "genomic" generally refers to data that both codes (also referred to as "genetic" data) as well as data that is non-coding. The term "genome" refers to an organism's entire hereditary information. Genomic sequencing is the process of determining a particular organism's genomic sequence.

The human genome, as well as that of other organisms, is made of four chemical units called nucleotide bases (also referred to herein as "bases" for brevity). These bases are adenine(A), thymine(T), guanine(G) and cytosine(C). Double stranded sequences are made of paired nucleotide bases, where each base in one strand pairs with a base in the other strand, according to the Watson-Crick pairing rule, i.e., A pairs with T and C pairs with G (In RNA, Thymine is replaced with Uracil (U), which pairs with A).

A sequence is a series of bases, ordered as they are arranged in molecular DNA or RNA. For example, a sequence may include a series of bases arranged in a particular order, such as the following example sequence fragment: ACGCCG-TAACGGGTAATTCA (SEQ ID NO.:3).

The human haploid genome contains approximately 3 billion base pairs, which may be further broken down into 23 pairs of chromosomes. The 23 chromosomes include about 30,000 genes. While each individual's sequence is different, there is much redundancy between individuals of a particular genome, and in many cases there is also much redundancy across similar species. For example, in the human genome the sequences of two individuals are about 99.9% equivalent, and are therefore highly redundant. Viewed in another way, the number of differences in bases in sequences of different individuals is correspondingly small. These differences may include differences in the particular nucleotide at a position in the sequence, also known as a single nucleotide polymorphism or SNP, as well as addition, subtraction, or rearrangement or repeats or any genetic or epigenetic variation of nucleotides between individuals' sequences at corresponding positions in the sequences.

Because of the enormous size of the human genome, as well as the genomes of many other organisms, storage and processing genomic sequences (which are typically separate sequences generated from a particular individual or organism, but may also be a sequence fragment, sub-sequence, sequence of a particular gene coding sequence or non-coding sequences between genes, etc.) creates problems with processing, analysis, memory storage, data transmission, and networking. Consequently, it is usually beneficial to store the sequences in as little space as possible. Moreover, it is typically important that no information is lost in storage and transmission. Accordingly, processing for storage or transmission of whole or partial sequences should include removing redundant information in a sequence in a lossless fashion.

Existing sequence storage techniques use coding for the four nucleotides (A, C, G and T) which may map them to characters in a text format. This sequence information may be further mapped to binary data. For example, A may be mapped to binary 00, C may be mapped to 01, G to 10 and T to 11 as shown in FIG. 1. Obviously, other encodings may also be used. These binary codes may be stored in a computer memory as arranged in the mapped sequence (as shown in FIG. 2), or in other arrangements.

FIG. 2 illustrates an example of this mapping and memory storage, where the illustrated memory is configured with 16 bit memory locations. However, other memory sizes and configurations could also be used. Five sequences, sequences 210-250 (SEQ ID NOS.: 3-D, are shown, along with associated memory mappings of the sequences in memory locations 210M-250M, which may be in a memory device such as DRAM, SRAM, Flash, CAM, etc., may be in a database such as on a hard disk drive, etc., or may be on storage media such as DVD ROM, Blu-Ray, or other storage media. In a memory or database, the information shown would require 5 times 40 bits or 200 bits. In this example the sequence size is very small, however, for typical sequences, such as a human sequence, each individual's sequence data would be approximately six billion bits long (i.e., about 6 Gb, or about 0.75 Gigabytes (GB)) if coded as shown.

Consequently, for a database having a relatively small number of sequence entries (for example, 1024 entries or 1K), the database size would approach one terabyte, which is impractical for storage, movement, processing, networking, or analysis for widespread use with current computing technologies. However, as noted previously, in genomic sequences within species (and in many cases across species) the nucleotide bases are typically very similar between individuals, normally having very small deviations. This characteristic of DNA may be used, as further described subsequently herein, to effect coding for compression of sequence data as well as perform other processing and output data generation and distribution functions These may include generating genomic specific instructions, performing further processing based on the genomic specific instructions, as well as implementing associated processing software and hardware.

Variations in the DNA sequences of different individuals are a result of deviations (also known as mutations). For example, one type of mutation relates to substitutions of nucleotide bases at common or reference positions in the sequence. A base substitution (also known as a point mutation) is the result of one base in a sequence at a particular position or reference location being replaced with a different one (relative to another sequence, which may be a reference sequence from which other sequences are compared). A base substitution can be either a transition (e.g., between G and A, or C and T) or a transversion (e.g., between G and its paired base C, or A and its paired base T). For example, sequence 1 of FIG. 2 has a transition, with reference to sequence 2, at position 20 (i.e., the G of sequence 0.2 is replaced with an A in sequence 1).

These seemingly simple and minor mutations are not biologically equivalent and can have significant biological implications and consequences. Transition mutations are more commonly observed and generally result in less deleterious effects on cells, while transversions are generally less common and may lead to more severe phenotypic effects.

In order to express the message encoded in DNA, an RNA copy of the genetic information corresponding to a single gene is translated into the amino acid sequence of the encoded protein. The RNA copy, called a messenger RNA (mRNA) is read by the ribosome in packets of three nucleotide bases called codons. There are 64 codons, of which 61 can be translated. The remaining 3 codons are not translatable and cause the ribosome to stop and disassemble and reinitiate translation of a new message. The 61 codons code for the 20 different amino acids found in proteins. Of the 61 codons, there are 19 codons that encode 10 different amino acids that can be mutated at the first, second, or third position to render that specific codon a non-translatable stop codon with a single base substitution. Of these 19 mutant codons, only 5 (coding for 3 different amino acids) result from transitions while the other 14 are the result of transversions. Table 1 lists the set of codons for which single base substitutions can cause conversion to stop codons.

TABLE 1

| Stop Codon | Tranversions | Transitions |
| --- | --- | --- |
| UAA | $\underline{AAA}^{(Lys)}$ $\underline{G}AA^{(Glu)}$ | $UC\underline{G}^{(Gln)}$ |
|  | $\underline{UU}A^{(Leu)}$ $\underline{UC}A^{(Ser)}$ | UGA |
|  | $UA\underline{U}^{(Tyr)}$ $UA\underline{C}^{(Tyr)}$ | UAG |
| UAG | $U\underline{C}G^{(Ser)}$ $\underline{A}AG^{(Lys)}$ $\underline{G}AG^{(Glu)}$ | $\underline{C}AG^{(Gln)}$ |
|  | $UA\underline{U}^{(Tyr)}$ $UA\underline{C}^{(Tyr)}$ $U\underline{U}G^{(Leu)}$ | $U\underline{GG}^{(Trp)}$ |
|  |  | UAA |
| UGA | $\underline{A}GA^{(Arg)}$ $U\underline{U}A^{(Leu)}$ $UG\underline{C}^{(Cys)}$ | $\underline{C}GA^{(Arg)}$ |
|  | $\underline{G}GA^{(Gly)}$ $U\underline{C}A^{(Ser)}$ $UG\underline{U}^{(Cys)}$ | $U\underline{AA}$ |
|  |  | $U\underline{GG}^{(Trp)}$ |

From Table 1, it may be observed that single base substitutions resulting in termination of translation are caused primarily by transversions. Thus transition mutations leading to a truncated protein product with negative effects are far less likely. An alternative way to consider this is that translation stop codons are important in defining the correct mature C-terminal end of proteins. However, stop codons can also be mutated to a codon that codes for an amino acid giving rise to a longer than intended polypeptide that will result in a reduced, null function or toxic product. Any base change of the type known as transversion at an existing stop codon will result a codon that encodes an amino acid; this will allow read-through, since the codon becomes translatable (see Table 1). The only base changes to an existing stop codon that result in preserving a stop codon at that position are transition mutations.

There are various types of substitutions. For example, one base at a particular position may be replaced by one of the other bases, e.g., Transition (G<->A or C<->T) and/or Transversion (G/A<->C/T). In a reversion, the mutation reverts to the original base (at the same or a second site, and the function may be regained). In a silent mutation, a single base substitution results in no change in the corresponding amino acid sequence in the protein being expressed. In a mis-sense multation, a base substitution causes a change at a single amino acid in a protein sequence. In a non-sense mutation, a base substitution that changes a codon specifying an amino acid to one of the three stop codons (UAA, UGA or UAG) thus producing a truncated protein.

In addition to substitutions, mutations may include insertions and deletions. It is noted, however, that other conditions, in addition to substitutions, insertions and deletions, can generate disease conditions. For example, re-arrangement of base sequences, addition of foreign sequences, triplet expansions, copy number variation, and other sequence variations and ordering manipulations may also occur and may result in expressed or unexpressed biological variations, disease conditions, and/or other abnormalities. Each of these types of DNA mutations can be acquired and manifested in different ways and may exert their effects in different or similar fashions.

As with substitutions, there are different types of insertions and deletions. Deletions may include single or multiple base deletions, which are generally randomly distributed in a DNA sequence and are a common replication error, which may result in frame-shift mutation if they are not a multiple of three bases. Excision deletions are larger deletions such as the case with removal of a transposable element. They may be integrated viral sequences or other repeat sequences. Excision deletions are generally precise events that are site directed and can lead to fusion proteins.

Insertions may be simple insertions, where single or multiple bases are inserted, usually at DNA replication. These are typically random events. Transformation insertions are insertions of any foreign DNA sequence in to a cell. In particular, conjugation is an integral part of insertions of bacterial DNA sequences into a host genome, and transduction insertions are insertion of viral sequences. Transposition insertions are insertions of a transposable element into a genome, which are capable of amplifying many copies throughout the genome. These are typically not random. Transposition may also include retrotransposons. Alu family insertions are a 300 base repeat sequence found in various numbers of copies in the human genome and account for about 10 percent of the genome. Insertions in Alu can result in colorectal and breast cancer, hemophilia, and other disease conditions. Cross Over insertions are rearrangements at the chromosomal level. These recombinant events can occur between different chromosomes or within pairs. Inversions are recombination events resulting in reversed polarity in a section of the inverted sequence. Splice site mutations can result in an alternative splicing event of the mRNA processing. Repeat sequences are base sequences repeated throughout the genome. For example, the CA sequence repeats in humans. These may be used in genotyping. SINEs are short interspersed repetitive elements that are non-reverse transcriptase coded and that may amplify bases of mobile elements. Both SINE and LINE are non-LTR (long term repeat) transposable elements. While both types of transposon are duplicated via an RNA intermediate, only LINE encode an enzyme that reverse transcribes the RNA transcript to give a DNA copy that is integrated in the host genome. SINE consists typically of less than 500 bases and, in the case of the Alu family, consists of Alu1 restriction endonuclease recognition sequences. LINEs are long interspersed repetitive elements that encode reverse transcriptase (e.g., RNA reverse transcriptase to DNA). Copy number variations are deletions or duplications of genes that may be associated with particular diseases. Aneuploidy is a sequence having an abnormal number of chromosomes. This may be associated with diseases such as Down's Syndrome. These define mutation events based on DNA (genomic or mitochondrial) or RNA or proteins.

Applications of Genomics Instructions

In one aspect, the above-described biological events, as well as others, may be represented in an instruction format with instructions associated with biological events, as well as other events or processing controls. In some embodiments, hardware, firmware and/or software may be used to perform associated functions. For example, a processor or other instruction processing device may be configured to perform processing using instructions such as are further described below. Likewise, memory or other data storage architectures or storage media may be used to store the instructions and provide them to processors or other processing devices. Encoded instructions may be stored in a computer product, such as a file or database on a computer storage medium. The encoded instructions may be further used to perform additional processing, such as for determination of characteristics or properties of organisms associated with the instructions or underlying sequence data.

One example instruction set includes instructions associated with the following biological events: transition, transversion, silent mutation, mis-sense, non-sense, deletion, excision, insertion, conjugation, crossover, and jump actions. Additional details of an example instruction set 300 for implementing these functions is shown in FIG. 3. It is noted that instruction set 300 of FIG. 3 is provided for purposes of illustration, not limitation, and other instructions sets including more or fewer instructions, instruction configurations, and other additions or variations may also be used in various implementations. For example, other instructions may include additional biological processing instructions and/or other processing instructions. In one implementation, the location within the nucleotide sequence may be implied based on the position of the instruction in the sequence (as explained further subsequently herein). Other instructions can obviously be added to those shown in FIG. 3, such as, for example additional insertion instructions, other manipulation instructions (for example, pointer movements), conditional related instructions (IF and FOR loops), and/or other instructions. In some implementations, instruction set processing as described herein can be combined with compression processing, such as is described in related U.S. patent application Ser. No. 12/828,234, incorporated herein by reference.

Some example applications of instruction sets are further described below.

Example Application 1

Encoding Single Nucleotide Sequence

An example of use of instructions for encoding a single nucleotide sequence representation is provided below. If it is assumed that information is understood for the specified nucleotide sequence, e.g., at a position 15 in the sequence there is a known single nucleotide polymorphism (SNP), the sequence can then be encoded with an instruction set which contains the biologically relative information in an instruction format.

Consider the example nucleotide sequence shown below (denoted as Sequence 1 (SEQ ID NO.:1)):

```
                    (Sequence 1 (SEQ ID NO.: 1))
     CCGGT_CCAGG_GGACG_CGACC_AAAAA_GCCCA
```

Assuming in Sequence 1 (SEQ ID NO.:1) that there is a transition at location 3 and a crossover event where the AAAAA should have been at location 11 (relative to a defined reference sequence), Sequence 1 (SEQ ID NO.:1) can be represented by the following instruction set (denoted as Instructions 1, based on the instructions as defined in Table 300 of FIG. 3);

JMPA 2;
TRANS G; (Instructions 1)
JMPR 7;
CROSS 5, 10

Conversely, from these instructions it can be determined that the sequence, if there were no mutations or modifications, would have been:

```
                    (Sequence 2 (SEQ ID NO.: 2))
     CCAGT_CCAGG_AAAAA_CGACG_CGACC_GCCCA
```

This describes that at position three in Sequence 1 (SEQ ID NO.:1) there should have been an "A," and the five nucleotide sequence "AAAAA" at position 21 should be at position 11.

Example Application 2

Comparing Nucleotide Sequences

Figure 4:
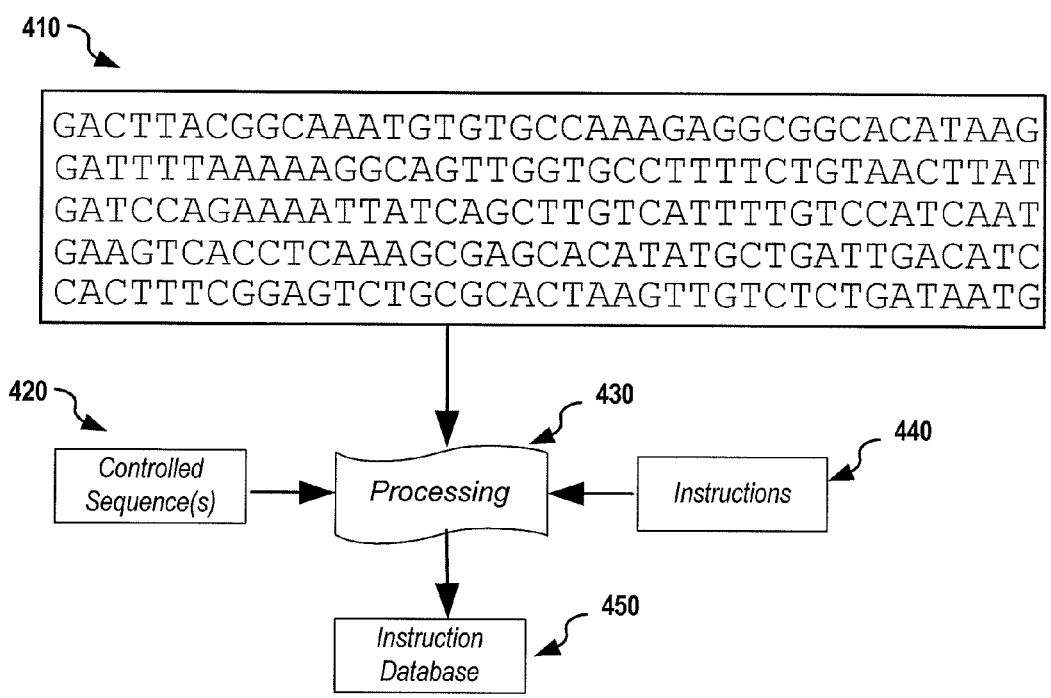
FIG. 4 illustrates one embodiment of a process for coding biological sequences (SEQ ID NOS.: 15-19) using an instruction set such as is shown in FIG. 3.

There are a number of applications where users may wish to compare a nucleotide sequence against other sequences. An example of this is shown in FIG. 4, where sets of sequences 410 may be processed in processing module 430 using a set of instructions 440, such as those shown previously in FIG. 3. By using a set of instructions, as shown in FIG. 4, the sequence may be encoded in an instruction-encoded format which may be stored in a database, such as database 450, a memory, and/or a computer storage media or other data storage device or apparatus.

In particular, as shown in FIG. 4, one or more controlled or reference sequences 420 (SEQ ID NOS.: 15-19) may be created or selected, which may be stored in a memory or database. The reference sequences may be created or selected as is described in, for example, U.S. patent application Ser. No. 12/828,234.

Figure 13:
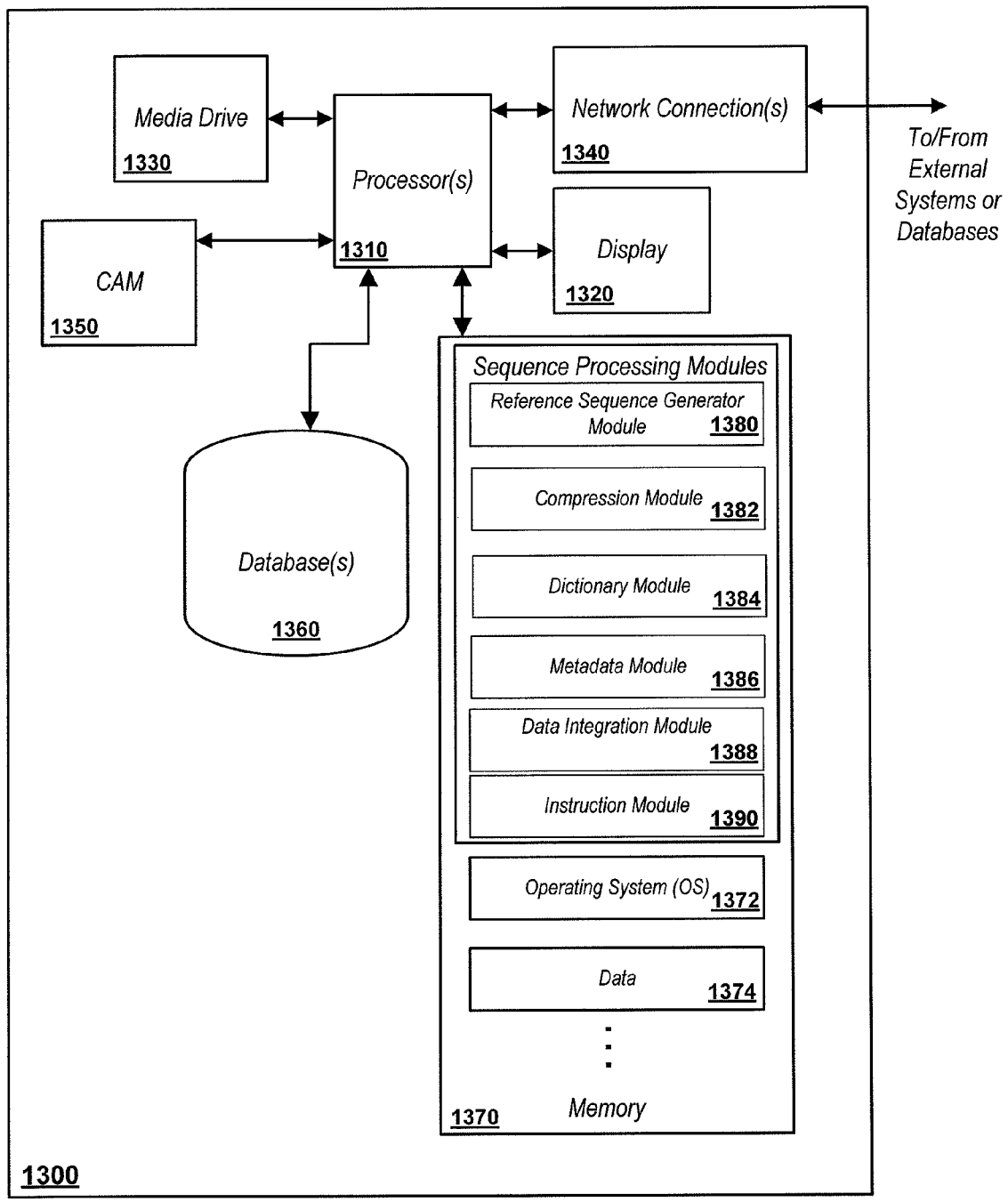
FIG. 13 illustrates an embodiment of a system for processing biological sequence data.

The database sequences 410 may be encoded based on the created or selected reference sequence(s) in processing module 430. This module may be part of a processing system such as shown in FIG. 13. An instruction set 440, which may be the same as or similar to the instruction set shown in Table 300 of FIG. 3, may be used for the encoding. The resulting instruction-encoded sequences may be stored in database 450, which may be the same database the original sequences 410 are stored, or may be another database. The instruction-encoded database may then be used for genomic processing, analysis, networking, data transmission, or other purposes.

Figure 5:
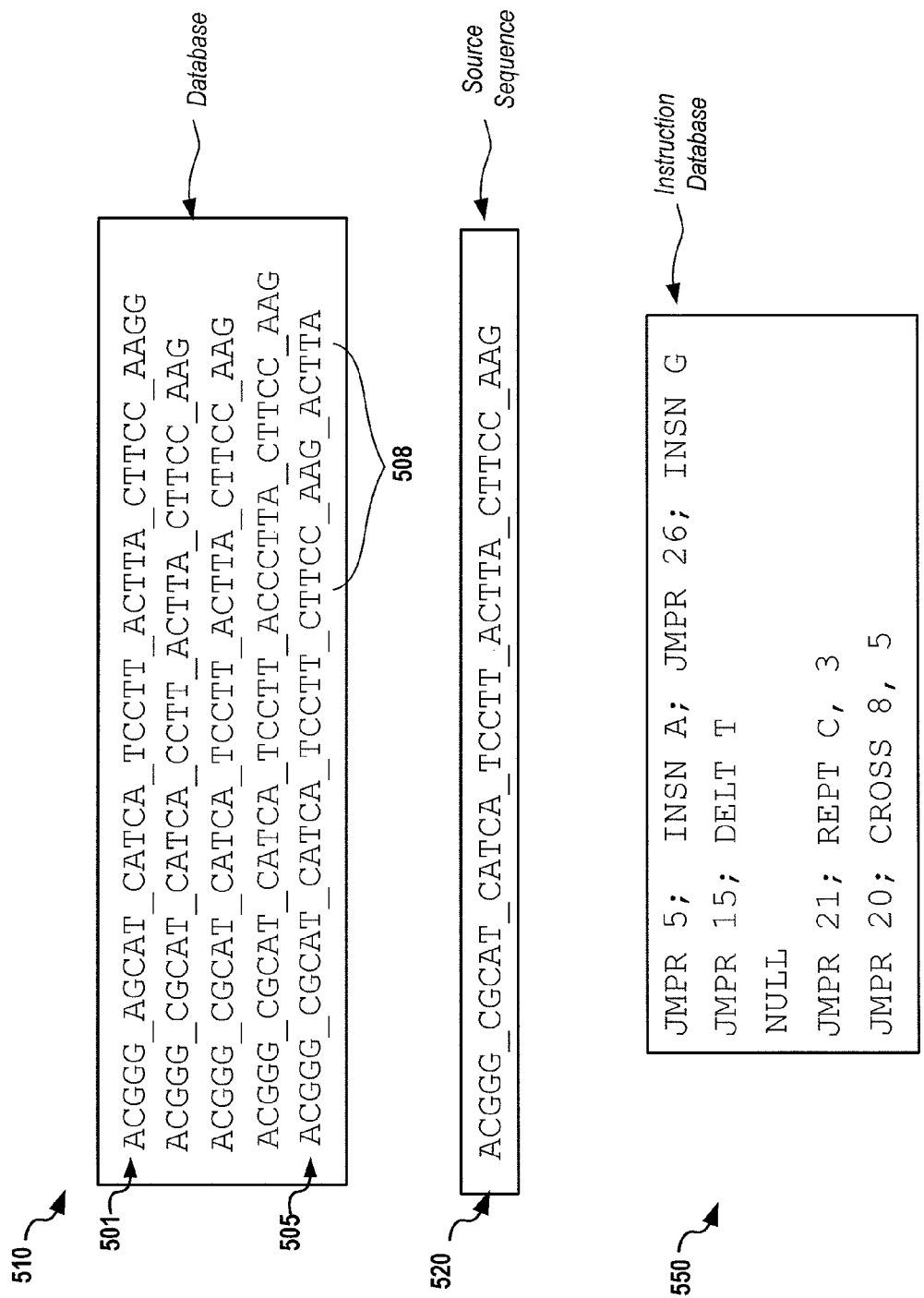
FIG. 5 illustrates an example encoding (SEQ ID NOS.: 20-24) based on the process of FIG. 4.

FIG. 5 illustrates an example of data coding consistent with this approach. As shown in FIG. 5, five nucleotide sequences 510 (SEQ ID NOS.: 20-24) may be stored in a source sequence database. For purposes of explanation, it is assumed that the middle entry is used for encoding (shown as source or reference sequence 520). Generating instructions may include determining differences between sequence 520 and the entries 510 of the database. The differences between sequence 520 and the other entries in 510 are minimal and can be readily seen in this example. Specifically, entry 501 has an insertion at position 6 and position 27. Entry 505 is equivalent to entry three, with the difference being a crossover event at the locations 508. In various embodiments, controlled, source or reference sequences may be generated in different ways, such as those described below and/or in U.S. patent application Ser. No. 12/828,234.

Example Application 3

Selectin a Controlled/Reference Sequence

In order to minimize the biological differences between the controlled, source or reference sequence and the database, it may be important to select an appropriate controlled/source sequence. One embodiment of reference sequence selection is shown in process 600 of FIG. 6. At stage 605, a source sequence database 680 is selected or accessed. Entries in the database are typically from the same species, however, in some cases entries may be from multiple species. One or more sequences from the database (typically a set of some or all sequences in the database) are then selected for processing. A reference sequence or sequences may be selected (or updated on subsequent iterations) at stage 610. The reference sequence may be selected or determined from entries in the database 680 or may be chosen from other sequences. In an exemplary embodiment, one entry from the database is initially selected and in subsequent iterations of the process, the feference sequence may be adjusted or updated, which may be subsequent to dictionary processing.

At stage 615, the database sequences may be compressed using an instruction set 690. Instruction based encoding may be implemented as described elsewherein herein, and the encoding may be based on the selected reference sequence or sequences.

Figure 6:
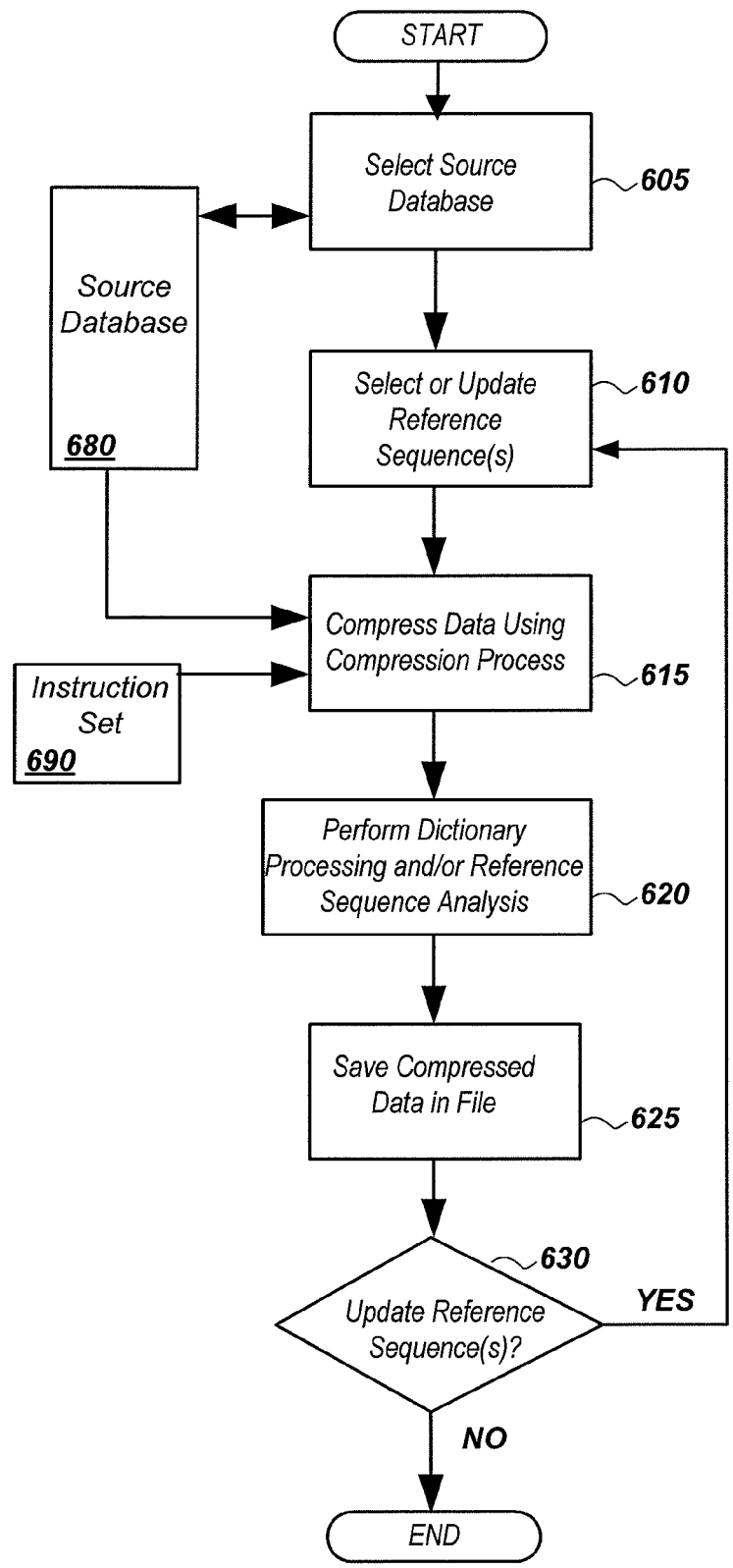
FIG. 6 illustrates an example process for coding biological sequences using instruction set coding.
Figure 7:
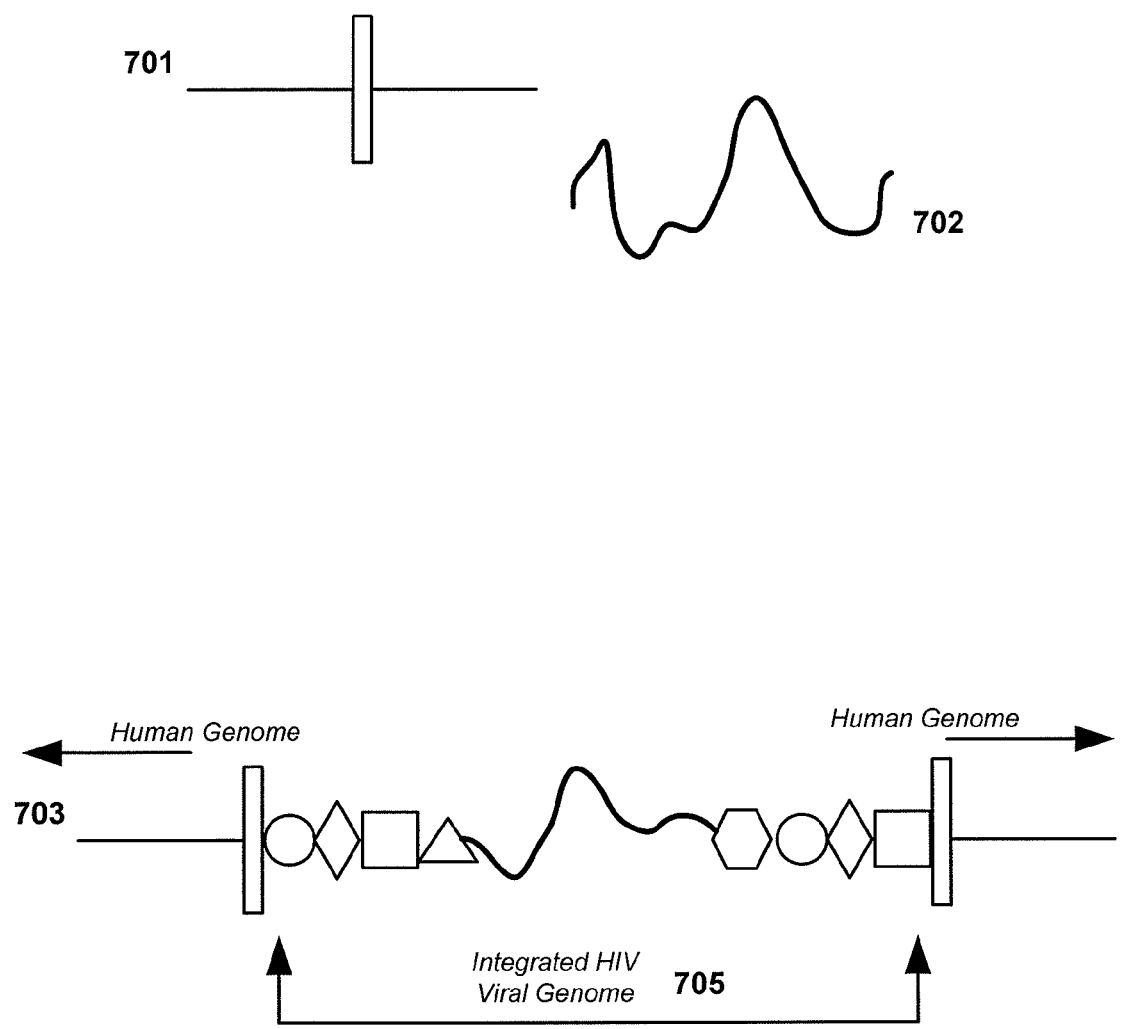
FIG. 7 illustrates details of an example insertion.

The instruction set may then be analyzed at stage 620 to perform dictionary processing and/or determine whether the reference sequence(s) should be changed, such as if further size reduction can be achieved. This may be done, for example, based on an analysis on a resulting encoded database to determine if the majority of the entries have the same instruction. For example, the controlled sequence may have a nucleotide base of "A" at location three, but the majority of the entries may have a "G" at location three. The resulting instruction database would then contain the transition instruction at location three. If this is the case, execution may be returned to stage 610 to update the controlled/reference sequence, such as, for example, by replacing the position three value of "A" with a value of "G." After updating on the controlled sequence the compression processing may be repeated. This may be done until there is no further need to update the controlled sequence, such as if a desired level of compression is achieved. This process may essentially reduce the controlled sequence with minimal mutations or deviations. In addition, metadata may optionally be added to the instructions. The metadata may related to clinical and/or pharmacological characteristics or information associated with the instructions and/or underlying sequences. The encoded instructions and any associated metadata or other information may be stored in a database, memory or other storage medium at stage 625. Process 600 may include a decision stage 630, where a decision may be made as to whether the reference sequence or sequences should be updated. This may be based on, for example, a count of dictionary entries determined at stage 620. Process execution may then return to stage 610 as shown in FIG. 6 for subsequence iteration.

footprint. In a simplified example as shown below, a basic instruction set may be assumed, i.e., an instruction set including transition, transversion, and deletion. It is apparent that other instructions and instructions sets may be used in various other implementations.

In a typical database, the genomic sequence would be represented as follows. Since there are four possible values a nucleotide base can have, each of these bases would be stored as a two-bit (binary) value. For example, the four bases may be represented as:

A=>00

C=>01

G=>10

T=>11

Other binary or non-binary configurations could alternately be used. If the database consists of the following five entries, a memory or other storage device would hold the binary sequence listed below:

```
Entry 1: ACGCCGTAACGGGTAATTCA or                              (SEQ ID NO.: 3)
         00.01.10.01.01.10.11.00.00.01.10.10.10.11.00.00.11.11.01.00

Entry 2: AAGCCGTAACGGGTAATTCG or                              (SEQ ID NO.: 4)
         00.00.10.01.01.10.11.00.00.01.10.10.10.11.00.00.11.11.01.10

Entry 3: ACGACGTAACGGGTAATTCG or                              (SEQ ID NO.: 5)
         00.01.10.00.01.10.11.00.00.01.10.10.10.11.00.00.11.11.01.10

Entry 4: ACGACGTATCGGGTAATTCA or                              (SEQ ID NO.: 6)
         00.01.10.00.01.10.11.00.11.01.10.10.10.11.00.00.11.11.01.10

Entry 5: ACGACGTATCGGGTAATACA or                              (SEQ ID NO.: 7)
         00.01.10.00.01.10.11.00.11.01.10.10.10.11.00.00.11.00.01.10
```

In some implementations, there may be more than one source/controlled sequence. In this case, the particular sequence used may be specified in the instruction database entry. For example, if two controlled/source sequences are used, entry one may refer to controlled sequence #1 while entry two may refer to controlled sequence #2. The first instruction in each entry may be in the form: Controlled Sequence, Num, where number (Num) represents the controlled sequence number.

Selection of Instructions

In various embodiments, the number of instructions in the instruction set may vary. In addition, the importance of the instructions used may be highly dependent on the application. In order to manage the instruction set so as to make sure the instruction database does not become unmanageable or inefficient, in some implementations a user may be provided an option to select which subset of instructions (from a larger set) are of interest. In these implementations, only the selected instructions may be used for encoding.

Certain biological events can be represented in one of several ways in a typical instruction set. For example, a substitution can be represented by a SNP or a transition instruction. If these two instructions were selected, there may be an ambiguity or redundancy in the instruction encoding. One way to address this is to use a priority selection. For example, the instructions may be assigned a priority, and if an event can be represented by multiple instructions, the instruction with highest priority may be used. Typically, the highest priority will be the instruction that contains more biological information or is more compact or otherwise more efficient.

Compression Example

One potential benefit of use of an instruction set for compression is being able to represent the database with a smaller For the five entries, the database size would 5*40 or 200 bits. In this example the database is small, but for a typical animal database, such as a human genome database, each entry would be approximately six billion bits long (~6 Gb or ~0.75 GB). If there were only 1024 (1K) entries, the database size approaches one terabyte of data. With current data storage and processing systems, this is generally too much data to store, move, process, network, transmit and/or analyze.

Accordingly, to address this problem, certain characteristics of genetic data may be utilized. For example, for a typical animal, such as a human, the difference between two sequences is on the order of $10^{-3}$ (i.e., 1 difference in 1000 bases). One approach involves establishing a minimum sequence for comparative biological referencing. One form of optimal minimum sequence may be established by first looking at sequences available in a database (i.e., entries) and choosing one that has a minimum average distance from other sequences in the database. Based on the data in the database it may make sense to have more than one minimum sequence template, so to generalize, N reference sequences may be considered. In some cases, the N reference sequences may be taken from entries in the database, but they may also be other previously identified or generated reference sequences. Examples of this are described in U.S. patent application Ser. No. 12/828,234. Having selected a reference sequence or sequences, instead of storing the corresponding full sequence information for every entry in the database, the index of the ideal minimum sequence and the instruction set from that reference sequence may instead be stored.

For example, using the example from FIG. 4 having five database entries, a difference vector for each entry may be calculated. The difference vector may be determined by the number of nucleotide bases at a given position that are different, as well as the value lost for deletions and insertions. The simple example below includes biological sequence database entries 1 and 2:

```
Entry 1: ACGCCGTAACGGGTAATTCA or                                (SEQ ID NO.: 3)
00.01.10.01.01.10.11.00.00.01.10.10.10.11.00.00.11.11.01.00

Entry 2: AAGCCGTAACGGGTAATTCG or                                (SEQ ID NO.: 4)
00.00.10.01.01.10.11.00.00.01.10.10.10.11.00.00.11.11.01.10
```

In this example, the nucleotide base in positions two and twenty are different (as shown in BOLD above), but all the bases at every other position are the same. The difference value in this example would therefore be two. Performing this calculation for all the entry combinations, the result is:

Entry 1 difference vector would be=>0, 2, 2, 2, 3 or an average of 1.8

Entry 2 difference vector would be=>2, 0, 2, 4, 4 or an average of 2.4

Entry 3 difference vector would be=>2, 2, 0, 2, 3 or an average of 1.8

Entry 4 difference vector would be=>2, 4, 2, 0, 1 or an average of 1.8

Entry 5 difference vector would be=>3, 4, 3, 1, 0 or an average of 2.2

From this we can see that entries 1, 3, or 4 would yield optimal sequences for biological referencing based on average score. To decide which of the three to utilize, we may choose the one that minimizes the maximum difference. For example, the maximum difference with entry 1 and entry 3 is three, while with entry 4 it is four. Entry 3 may be selected for further explanation as the initial reference sequence (but entry 1 may also be used).

At this stage, two additional steps may be taken. The first step may be used to insure that an ideal minimum sequence is used for referencing, and the second may be the development of a biologically relevant programming language that can be utilized for optimal high-fidelity organization and storage of the data. This approach focuses on biological instructions that can be used to operate on each entry of the database.

Other implementations may use simple scripts to show replacement, addition or removal of bases at certain positions in the entry. This is a simple and inefficient method when representing highly complex molecular biological events that often times result in major structural rearrangements. For example, there are several types of single base substitutions, deletions, and insertions and each of these different types can have very profound biological effects on a cell and or the organism.

To establish one ideal minimum sequence to be used for referencing, a multipronged iterative process, such as is shown in FIG. 6, may be used. Applying this approach. The database would look as follows:

```
Reference sequence => ACGACGTAACGGGTAATTCG or       (SEQ ID NO.: 5)
00.01.10.00.01.10.11.00.00.01.10.10.10.11.00.00.11.11.01.10

Entry 1:   JMPR 3; transversion C; JMPR 15; transition A

Entry 2:   JMPR 1; transversion A; JMPR 2; transversion C

Entry 3:   Null

Entry 4:   JMPR 8; transversion T, JMPR 10; transition A

Entry 5:   JMPR 8; transversion T, JMPR 8; transversion A,
           JMPR 1; transition A
```

Converting this database to a three bit instruction opcode, a four bit address (addr) value and a two bit base, the database would be nine JMP and nine substitution instructions, which can be represented as 40+9*7+9*5 or 48 bits. Even though, in this example, the reduction is only approximately 25%, with a real genomic database the reduction would be much higher for several reasons, including: 1) in this example, the difference on average is 2 base positions out of 20. This means 90% similar between the sequences. The human genome sequence, however, is closer to 99.9% similar; the source sequence accounts for a large percentage of the total number of bits. This is because the number of entries in this example is five. If the number of entries was one million, then number of bits of the source sequence is insignificant; 2) an optimal source sequence or sequences can be generated as described herein. In some implementations, multiple source sequences may be used; 3) additional biological instructions, e.g., crossover, etc., may also be used; 4) address mapping may be used to reduce the address space further, i.e., the addresses may be mapped from one domain to another.

Using this approach, all original sequence data may be retained, including the reading frame, which allows for processing and analyzing the proposed organization of the data.

Below is an example showing the effect of source/reference sequence selection. The sequence used to calibrate the data does not have to be one of the entries in a source database. It could simply be generated or initially assigned by looking at the common entry for each of the positions. For example in position two every entry has a C except the second entry, which contains an A. In order to develop a minimum sequence a C could be added. This is an example of recursive purification of the ideal sequence used for referencing. Doing this for every position may result in an ideal minimum sequence, and the corresponding compressed database as shown below:

```
                                        (SEQ ID NO.: 8)
Biological referencing sequence:
ACGACGTAACGGGTAATTCA Entry 1: =>       JMPR 3; transversion C Entry 2: =>       JMPR 1; transversion A; JMPR 1;
                  transversion C
                  JMPR 15; transition G Entry 3: =>       JMPR 8; transition G Entry 4: =>       JMPR 8; transversion T Entry 5: =>       JMPR 8; transversion T; JMPR 9;
                  transversion A
```

The instructions database now contains eight JMPR and eight point mutation type instructions. This simple step reduces the database by a factor of ten percent (10%). Taking this approach one step further, addresses can be remapped. For example, there are only six unique addresses represented. These can be remapped to unique values. The instructions of the JMP could also be remapped to include the distance into the opcode. The substitution instruction may also be remapped to include the nucleotide base. Other remappings may also be done based on common or redundant data or information.

In the previous compression example, it is assumed that all the sequences are of the same length. Unfortunately, in general, actual biological sequences, such as DNA sequences, are not all the same sizes (i.e., don't have the same base length). In addition to nucleotides being changed at a particular position, there may also be many different types of inserted or deleted sequence elements with various biological relevance and disease associations.

For example, integration of HIV virus sequence information into the human genome may be considered as analogous to an insertion event in one of the entries in the database. In this case, the specific insertion may be managed and represented in the following manner.

Since the viral genome sequence is almost $10^4$ bases, a typical script for insertion at each viral base position would be an inefficient means to represent this type of insertion event. Using the example approach described below, at the insertion site the current positions would align with the controlled source sequence, but as soon as the HIV sequence is encountered it would be apparent that the particular entry no longer aligns with the source. This is shown in FIG. 7.

Upon encountering a stretch of non-aligning sequence, an instruction can be used to jump a specific number of bases, for example a hundred bases, and start alignment again. If the inserted sequence is still unable to align with the controlled then the jump may be made for a larger number, such as several hundreds or thousands of bases until alignment is achieved. The specifically selected jump instruction can then be used to identify the nature of the insertion. For example, if after a 300 base pair jump the entry is able to realign with the reference then it is unlikely to be an HIV viral integration. The jump length, in effect, provides information about the nature of the insertion, such as a possible type of insertion. In this case different addresses may be looked up for short interspersed repetitive elements (SINE). For example, the insert may be a retrotransposon, like the Alu Family, which is about 300 bases long. This information, such as the jump length, may be further used in subsequent processing using the encoded instruction set.

However, if after the instruction to jump several thousand bases there still exists an inability to align with the ideal sequence used for referencing, then the inserted sequence can be probed for sequence elements that have viral association for this example. Alternatively, the inserted sequence may be a result of a crossover event, which would indicate that this inserted sequence is a human genome sequence from a different region of the same chromosome or a different chromosome, and could be present in a 5' to 3' orientation or a reverse polarity (3' to 5') in the case of an inversion. Other events and associated matching may also be determined and used.

As one example, the U3 and U5 regions of the HIV genome are unique sequences that can be used as markers to identify this inserted element as a virus sequence and these viral genome sequences can be held in a memory or other storage element with a specific address. Using instructions it may then be possible to look up the address and determine if this sequence belongs to the suspected HIV genome (or other genomes) as well as, in addition, specifically which strain.

Additionally, the viral repeat sequence (which is normally referred to as R and indicated by diamonds in FIG. 7), the primer binding site, and the polypurine tract are all sequence recognition elements that may be used to determine if the insert is an HIV viral genome (see, e.g., FIG. 7).

Chromosomal rearrangements are a component of major recombination events that may be encoded by a biological sequence programming language and associated instructions. These rearrangements can result in, for example, a deletion, inversion, and/or a translocation. All of these events involve DNA sequence information being moved from one location to another. Even though there might not necessarily be a net loss of genetic information in the case of inversion or translocation, the outcome can often be very similar in mutational effect to a deletion.

For example, consider a gene that is located at the site of the inversion or translocation. As we move from the 5' end towards the 3' end we will arrive at a position where the gene sequence is disrupted. This disruption of a certain gene can contribute to development of some types of cancer.

Chromosomal rearrangement events that result in the deletion, inversion or translocation could influence the integrity and expression of a gene at the site of this type of recombination. For example, if the event is a deletion of the 3' end of a gene then the resulting polypeptide produced will have a truncation at the carboxyl terminal end. This type of event is commonly known to have negative effects on the activity of the gene product, reduced activity or a null. An inversion at that site of the gene would generate a polypeptide where the amino terminus (N-terminus) appears to be normal in the sequence of amino acids up to the site of the inversion then the following series of amino acids from that point to the C-terminus would be random.

Returning to FIG. 7, additional details of the insertion event are illustrated. In this example, integration of HIV viral genome into the human genome sequence is shown as an insertion in an entry in the database. Item 701 is a graphical representation of one entry sequence in a sequence database, such as database 1380 of FIG. 13. In this block, the vertical bar is an indication of the site that will be the insertion site. Since the insertion event has not yet taken place, the DNA sequence is entirely human genome sequence in this region of DNA. Item 702 shows an example of the entire HIV genome sequence. This is a double stranded DNA copy of the HIV viral RNA genome sequence prior to integration into human genome. All the sequence elements that are indicated by special symbols in Item 703 are present in this representation of the complete HIV genome Block 702 (symbols are not shown for clarity). In Item 703, a DNA copy of viral genome has been integrated into human genome target sequence. The vertical bars on either end flanking the viral DNA are human sequences that have been duplicated as a result of the integration process. These bars represent a two base duplication of the original insertion site. The circles represent a region of viral DNA sequence that is called U3. U3 is a region of unique 3' end sequence that is used as a promoter for viral gene expression. The region generally referred to as R indicated by diamonds in this figure is viral repeat sequences. U5 is represented by two squares is the 5' unique sequences that is recognized by the viral protein integrase which is involved in the formation of a pre-integration complex. The triangle shape represents a region known as PB which is the primer binding site where the human tRNA is recruited to prime the reverse transcription of the RNA viral genome. The hexagon is a region known as PP or the polypurine tract and it serves as the initiation site for second strand synthesis. The curved line 720 is a representation of the remainder of the HIV viral genome that encodes all the required viral proteins for completing the life cycle of the virus including glycoproteins for packaging and maturation of viral particles.

For a translocation event, the same is essentially true except in the case where the fragment of DNA that has been translocated to that site belongs to the 3' end of another gene. This type of rearrangement will typically generate an oncogene fusion protein in the case of these chromosomal aberrations and is generally associated with cancer (see, e.g. FIG. 8, which illustrates an example).

Figure 8:
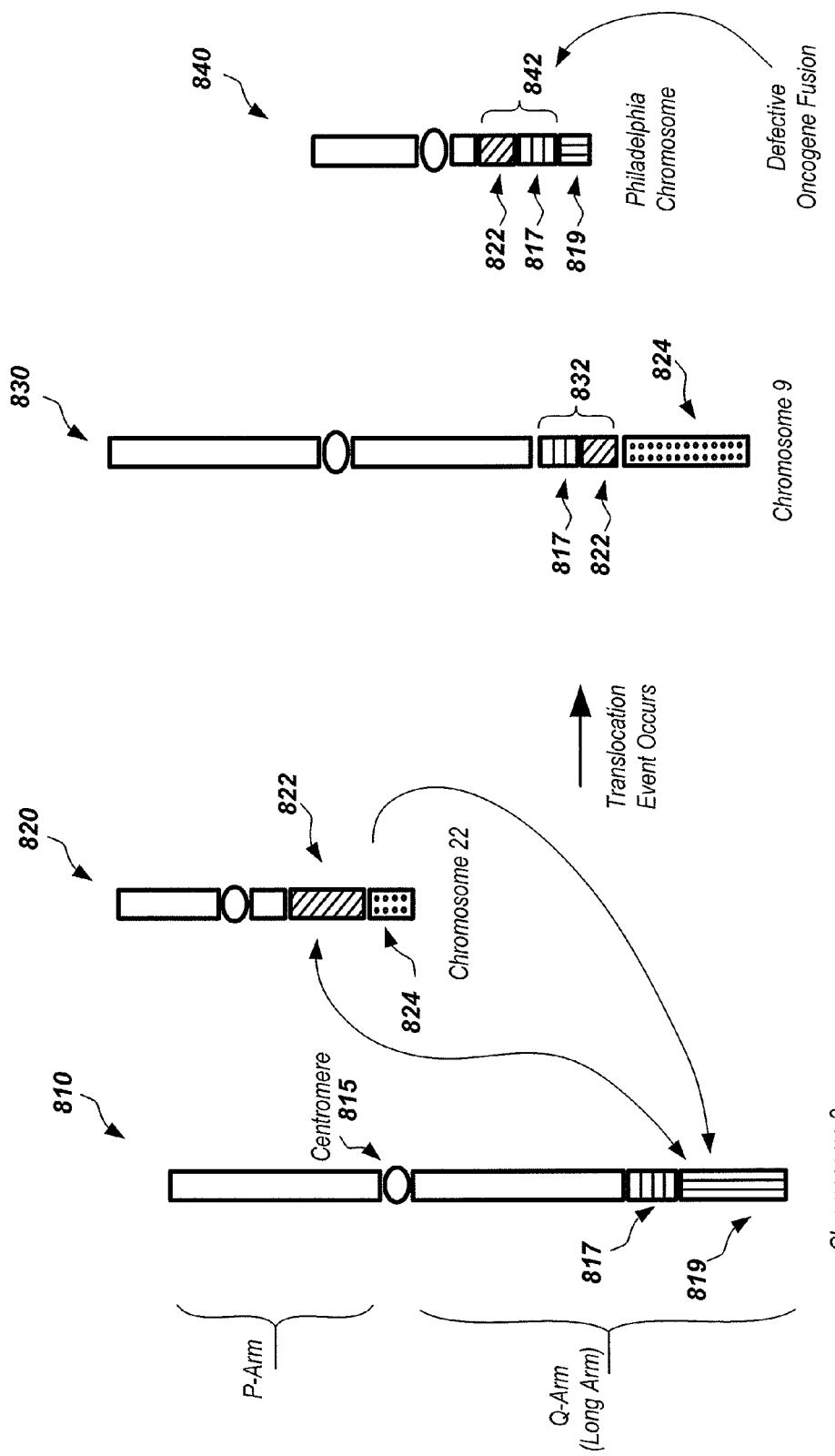
FIG. 8 illustrates details of an example chromosome rearrangement.

In some embodiments, instructions for programming the features for deletions may be a useful instrument for discovery and evaluation of these defects, as, for example, may be seen in cri du chat which will result from deletion of the p arm of chromosome 5, or in the case of chromosomal rearrangement between chromosome 9 and chromosome 22 for Philadelphia chromosome, as shown in FIG. 8.

Turning to FIG. 8, details of an example of a particular chromosomal rearrangement event, commonly known as a translocation, are illustrated. This is only one example of the type of event that comprise a descriptive DNA mutation event that may be used in an instructional programming language in accordance with the present invention, and the invention is not limited to this or any other particular chromosomal defects.

In a translocation, parts of different nonhomologous chromosomes are rearranged and joined or fused. FIG. 8 depicts four chromosomes as shown in panels 810, 820, 830 and 840. Each chromosome includes a short arm or p arm, a centromere, and a long arm or q arm. Centromeres, which are depicted as ovals in FIG. 8, join the long arm to the short arm. In panel 810, an example diagram of chromosome 9 is shown, with the chromosome having a target gene indicated by region 817 on the long arm of the chromosome. Centromere 815 separates the p arm from the q arm. A translocation site is located somewhere in 817. Region 819, at the tip of the q arm, represents the remainder of the chromosome and is also translocated in this example along with a fraction of the 3' end of the target gene in region 817.

Panel 820 illustrates a second chromosome (i.e., chromosome 22) involved in this particular translocation event. As with panel 810, the centromere is indicated by an oval. The target site for translocation is a gene indicated by region 822 of the q arm of chromosome 22 as shown in panel 820. Region 824, which represents the remainder of the chromosome, is located at the tip of the q arm (22q), and this region of DNA is also involved in the translocation event. This is the normal state of chromosome 22 prior to the translocation event.

Following occurrence of a recombination event, the two chromosomes exchange all or part of the illustrated regions of the respective chromosomes. In this example, the 5' end of the original target gene 817 in chromosome 9 is joined with the 3' end of gene 822 from chromosome 22. This results in region 832 shown in panel 830. In addition, the balance of the q arm of chromosome 22 (i.e., region 824) is translocated along with the 3' end of the target gene. The post translocation region 832 remains covalently linked as a contiguous part of chromosome 9 and the gaps shown in panel 830 are included for clarity.

In panel 840, the resulting defective form of chromosome 22 following rearrangement is shown (this is commonly known as Philadelphia translocation or Philadelphia chromosome). A sizable portion of the 5' end of the original gene from region 822 along with the 3' end of the gene from region 817 are fused in gene 842.

Several additional descriptive examples are provided below. In the first example, a single sequence of DNA from a database such as the Genbank at the National Center for Biotechnology Information (NCBI) is considered. Each sequence of DNA entry in such database will have, in addition to the actual sequence, additional information that is known or can be determined about the sequence. At NCBI, acquiring a certain entry sequence from the database will generally provide, at the minimum the base sequence and the size of the molecule, as well as how many bases are contained in this sequence. In addition, some additional information in the form of annotations or metadata may be provided.

Using a set of instruction such as those described above, which may grow and evolve in various embodiments, DNA may be programmed in such a manner that some or all elemental features would be descriptive. For example, whatever can be described in the characterization of a sequence of DNA, a biological instruction set of this language along with proper operation codes may be able to articulate any feature or element or structure or function or genetic component which is known or can be predicted or can be learned about a sequence of DNA (or other biological sequences).

For example, if the entry sequence taken from the database is known to be ten thousand nucleotide bases long and it is known that it codes for a protein, then we may know the actual sequence of bases in this entry, and knowing that it is a gene that encodes a protein it would be expected that some other fundamental information will be available. The source organism will generally be known which will give some indication of the likelihood of the existence of introns, for example. Some or all of the features may be known, such as, but not limited to, sequence elements such as promoter region, start and stop codons, transcription start, restrictions sites, ribosome binding sequence, polyA signal, splice junctions if eukaryotic source, synthetically assigned unique sequences, in addition to other common elements of a gene, that will express a protein product.

When using instruction-encoded sequences to compare the sequence elements present in one database entry versus another, the instruction set may expand to include more advanced operations and become increasingly diverse with regards to the details of the programming for that comparison of DNA sequence. This may be as a result of a learned or iterative process. For example, when two sequence entries are compared with each other users may have an opportunity to take advantage of how they relate to each other to improve the program functionality. Two entry sequences that are compared may have similarities and differences that become intimately involved in programming DNA sequence data. For example, in this case one sequence as relates to the other may allow for one entry to serve as the control sequence, which then provides an opportunity to use a biological programming language to compress DNA sequences based on the relative differences using biological instructions, such as described previously.

Where two sequences share sequence similarity, their differences usually have meaningful biological implications. In this case, a biological programming language may provide a unique advantage by using instructional operations relating to these changes in one sequence in comparison to the next. For example, the comparative analysis of two sequence entries with a specific set of biological instructions provides a way to organize these DNA sequences in a manner that is completely flexible and based on scientific knowledge.

A rearrangement of one region of the sequence with respect to another may be programmed based on the biological relevance. An insertion in one entry versus the next may have very different biological implications when the DNA recombination is as a result of a viral integration or a translocation event among chromosomal DNA. In this way, a biological programming language may allow a user to take advantage of scientific knowledge about the sequences that are being programmed. This may allow the language to be used as an analytical tool that, instead of comparing based purely on primary sequence information, alone allows further functional analysis. In this regard a biological programming language may use specific instruction sets that organize the DNA sequence data using scientific knowledge and biological relevance in combination with comparative sequence analysis.

The programming of two sequences as they relate to each other may become more powerful as a result of implementations of the processing and encoding described herein. By using biological knowledge to organize and relate two sequences, the capability to give biological intelligence to the data set may be provided.

Below are provided some additional examples for using an instructional approach to comparative analysis and description of two DNA sequences. This approach is not limited to DNA and RNA sequences but instead can be used to program lipids, polysaccharides, polypeptides and any other chemical or biological polymer. In the specific case of DNA, commonalities and differences in the biological sequence elements may be used to develop and enhance the scientific organization of the data for specialized processing. If the two sequences are identical, then the length and primary nucleotide base sequence of one need only be known, with the sequence of the other then known as well, and no instruction would be necessary.

In the case where two sequences are the same except for a single mutation event the second sequence can then be represented by a single instruction since the first sequence is known. This instruction, along with knowledge of the initial sequence, provides a scheme for a scientific description and compression of the two sequences. For example, the sequences may be:

```
                                             (SEQ ID NO.: 9)
Seq. #1. GGGGG GGGGG GGGGG GGGGG GGGGG GGGGG (SEQ ID NO.: 10)
Seq. #2. GGGGG GGGGG GGGGT GGGGG GGGGG GGGGG
```

Sequence 1 may be a polyG oligonucleotide that is 30 bases long while the second sequence is essentially the same with a single base change at position 15 (shown in BOLD above). Knowing the sequence and length of the first sequence, the second sequence can be represented with one simple instruction, such as:

Seq. #2. Transversion 15T

Accordingly, using one biological instruction it is known that there is a transversion at position 15 when compared with the first sequence (or a source or reference sequence). This also describes that all other positions are identical. We also know that position 15 was substituted with a T since the instruction is a transversion to a T and the source controlled sequence is a polyG oligo.

Now consider a third sequence (Sequence 3) that is 3,000 bases long:

```
                                             (SEQ ID NO.: 11)
Seq. #3.
GGGGG GGGGG GGGGT GGGGG ------------- GGGGG GGGGG
```

Here, the segment of Sequence 3 represented by the dashed line is a known sequence that belongs to a particular strain of the influenza virus (e.g., H1N1). When compared to the first sequence a second instruction may be used to represent the viral integration, such as:

Seq. #3. Trv 15; Intgr 21 H1N1

If a comparison is made between Sequence 2 and 3, then Sequence 3 can be represented as:

Seq. #3. Intgr 21 H1N1

If the specific influenza strain is known, the entire nucleotide base sequence of Sequence 3 may be reconstructed from this instruction-based version.

Implementations of a genomic programming language can be used, for example, with a specific instruction set for description and in analysis with unique DNA sequence elements involved or associated with certain diseases. For example, the sex chromosome common to both males and females is the X chromosome. There is a gene on the long arm of the X chromosome where a CGG tandem repeat sequence in excess of a certain number can be a marker for a carrier of or diagnosis of a Fragile X Syndrome. Fragile X causes mental retardation with increasing severity proportionate with the increase in the number of tandem CGG repeats in the FMR1 gene. An example is shown below:

(SEQ ID NO.: 12)

5'----------CGG CGG $(CGG)_{200}$ CGG CGG-----------3'

By using genomic programming language instructions for other features up to the Fragile X Mental Retardation 1 gene additional expansion instruction may be used for the triplet expansion, such as shown below.

Position relative; expn 200

Here, the dashes are indicative of the DNA sequence of the FMR1 gene upstream and downstream of the CGG expansion site in this gene. That is to say, when compared to the controlled or biological reference sequence this particular entity would use the instructions to describe features of this sequence on either side of the expansion region. Within the expansion site an expansion instruction would be invoked, such as:

Position relative; EXPN CGG 200 or

Repeat Triplet 200 (if, for example in this case 4 CGG was a normal condition).

In a second example of application specific DNA programming instruction sets and associated processing, splices may be considered. The mRNA transcripts of most human genes usually have introns that are spliced out in order to join the correct set of exons together. Sequence elements at splice donor and splice acceptor ends and highly conserved base sequence features of the introns are involved with splicing. During mRNA processing, the molecular environment regulates the splicing of the different exons in different tissues. Alternative splicing and expression of multiple combinations of exons is a way to build several variations of function sets from one gene. A DNA sequence may be programmed based on alternative splicing and the splicing code.

Defects in the alternative splicing process have been associated when comparing normal tissue exon expression and tissue from colon, bladder, prostate, and breast cancer, i.e., defects in the alternate splicing are indicators of these cancers. Using a set of instructional operations for splicing, the various alternative splice events may be accounted for. For example, highly conserved splice donor sequences for the expressed exon and splice acceptor end sequence may apply a jump instruction across introns and exons that are spliced out of the message, as shown in the example below:

Instruction for splice event #1
Splice 1, 2, 3
For splice event #2
Splice 1; Alt splice 2 (or splice jump exon 3)

Figure 9:
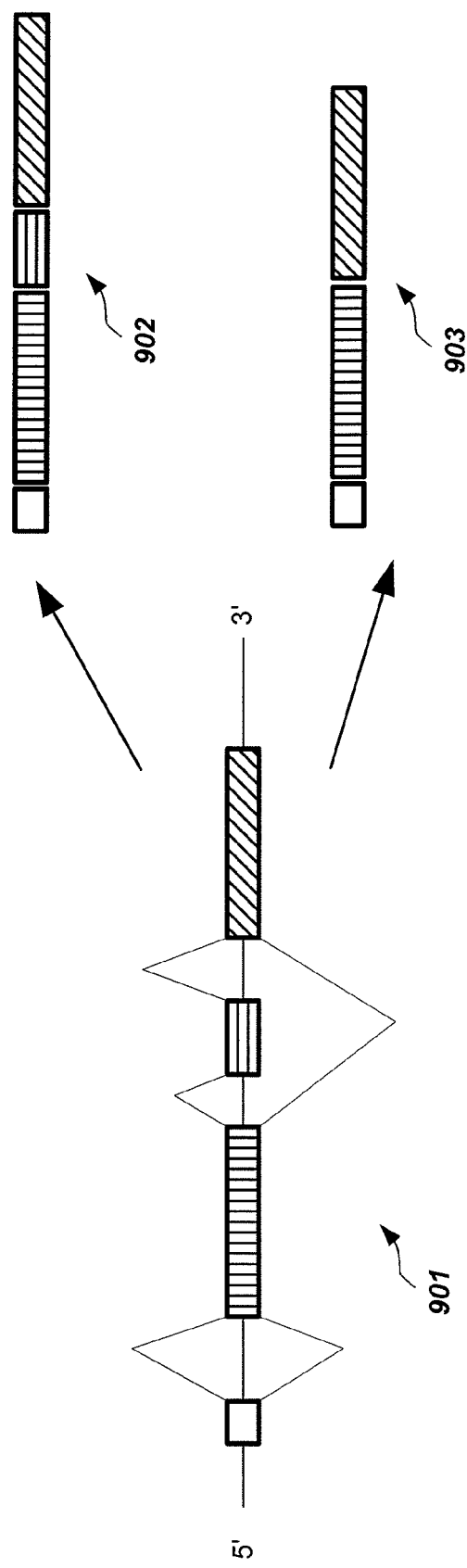
FIG. 9 illustrates details of example alternate splicing of mRNA.
Figure 10:
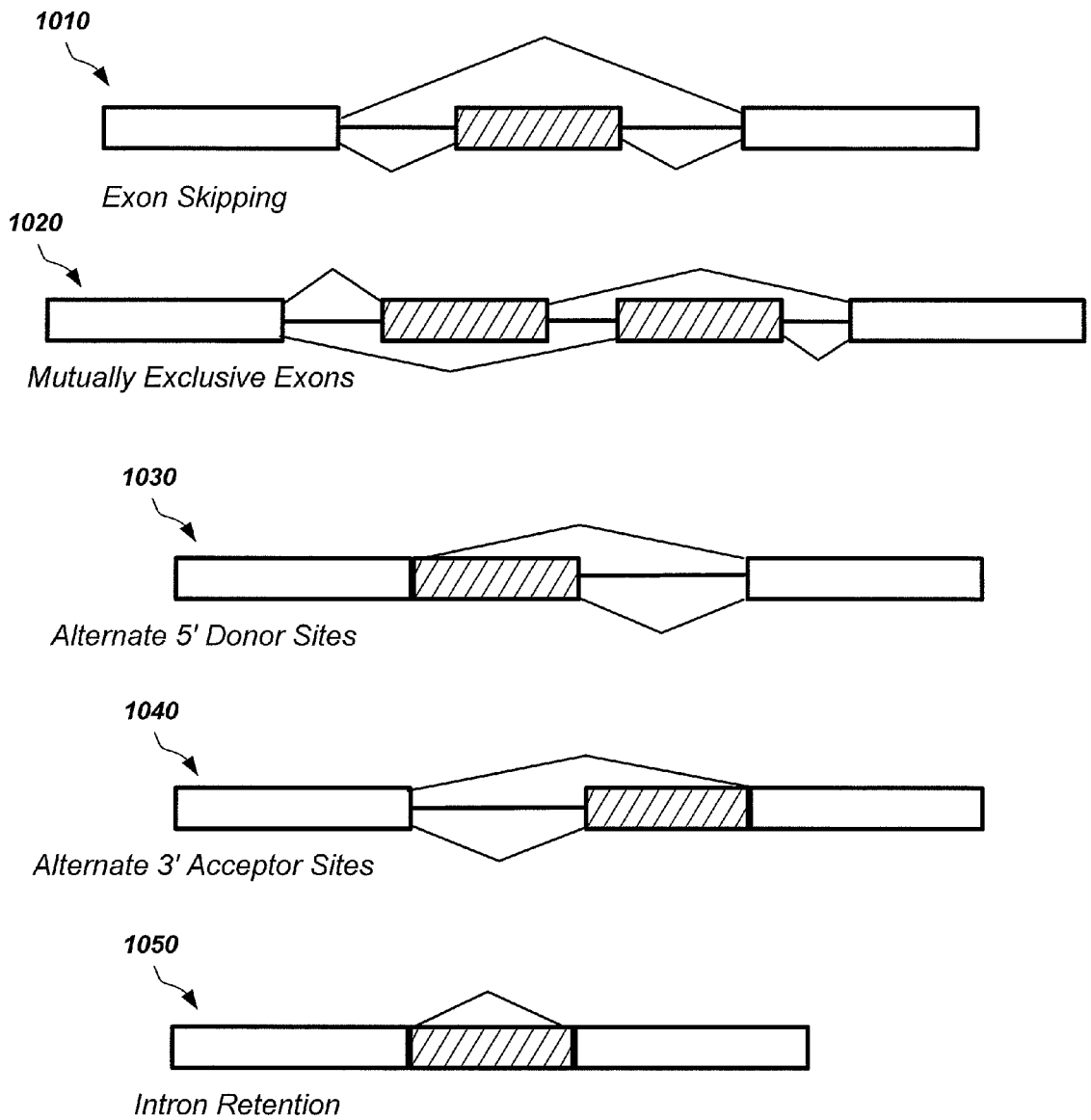
FIG. 10 illustrates details of examples of recombination.

Splice site donor is a highly conserved dinucleotide of sequence GC or GT. However the splice site donor GYNGYN is found across phylogenetic spectrum (where Y is C or T and N is any base). In addition to skipping exons, splice donors can occur within exons. A separate instruction may be used for this type of alt splice, in place of or in addition to the others. Examples are shown in FIG. 9 and FIG. 10, which are described in additional detail subsequently herein.

For example, looking at entry 6 and 7 below, it can be seen that besides position 3 changing from a G to a C, the third G in position 8 (highlighted in Entry 6) has been deleted in Entry 7.

```
Entry 6: ACGTAGGGCATTGCA    (SEQ ID NO.: 13)

Entry 7: ACCTAGGCATTGCA     (SEQ ID NO.: 14)
```

Figure 11:
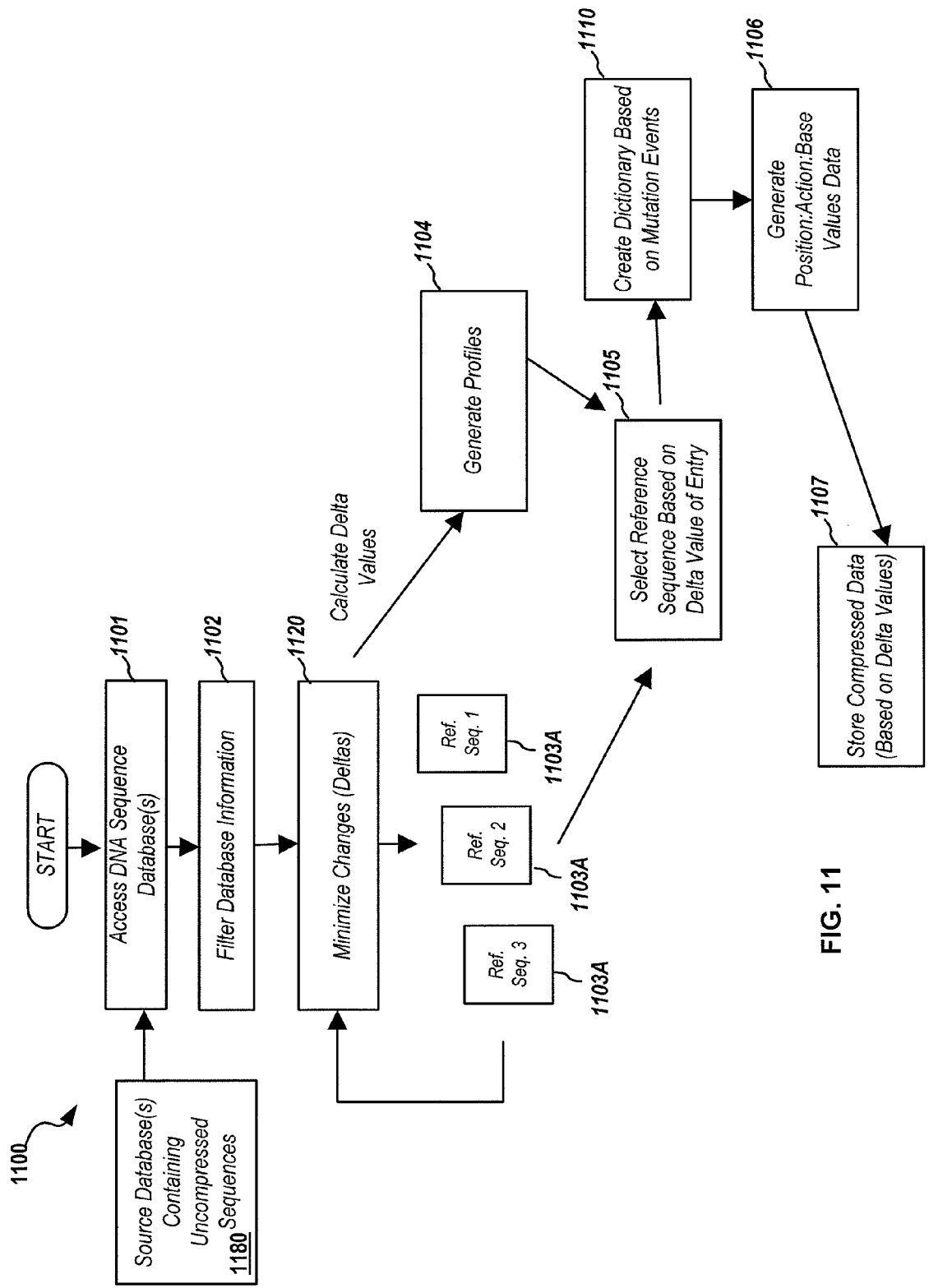
FIG. 11 illustrates an embodiment of a process for compressing of biological sequences.

The same procedure as described previously can be used, but additional information may also be added. For example, instead of having <position.value> being the delta information stored, <position.action.value> can alternately be stored. As an example, in one embodiment action may take the following values:

00->No operation/not used
01->Substitute the base value at the position address
10->Delete the base value at the position address
11->Insert the base value at the position address
100->Repeat the same nucleotide sequence starting at position up to value
101->Repeat and then invert the same nucleotide sequence starting at position up to value
110->Repeat the nucleotide base at position for value times
111->Reserved Attention is now directed to FIG. 11, which illustrates details of an embodiment of a process 1100 for compressing and storing sequence data using a delta database, such as database 1180. At stage 1101 a DNA sequence database contains data from an individual species; i.e. human genome DNA sequence. At stage 1102, the sequence entries in the source database may undergo a quick pre-processing procedure to determine two things: 1) Does this dataset fit the user's criteria for coding DNA based on threshold of similarity in the dataset? An example of a user defined criteria for DNA sequence instruction programming might be a predetermined maximum value for the highest variation value allowed for any one entry in the database against a selected minimum source sequence. Another example of the type of criteria that could be set by a user would be where the user is interested in operating on bacterial and viral DNA sequences only, in which case no entry in the database would be expected to be greater than the order of $10^7$ bases. 2) What are the most suitable minimum sequences that can be used for referencing based on these biological instructions? An experiment approach may be used to determine a best choice of a controlled source sequence. One approach to find a sequence for use in biological referencing is to run an alignment algorithm to determine which sequences have best correlation with the other sequences. For example, the sequences may be compared against each other and a Basic Local Alignment Search Tool (BLAST)—like algorithm may be run to determine the best average e-value. A BLAST algorithm finds regions of local similarity between sequences by comparing nucleotide or protein sequences to sequence databases and calculating the statistical significance of matches. A simple approach is to pick any sequence as the reference, run an algorithm to compress, and based on the results then make adjustments to the sequence, taking an iterative approach to the controlled source sequence refinement and purification.

It is expected that knowledge of the type of data contained within the database will be useful for determining suitability and efficacy of the instruction set format with regards to data structure. The degree of relative compression that can be achieved using this instructional approach may be directly related to the relatedness of sequence entries in the database. Therefore, for a database with a million entries of influenza virus or a particular human gene (BRCA1 for example) a known sequence for biological referencing could be selected. The minimum delta values for this may determine that a choice of sequence is suboptimal for a compressed organization of the dataset. Alternatively, a more suitable sequence can be generated or assigned as the source database is pre-processed. Using CAM allows fast and efficient parsing of databases with million deep entries.

It may be difficult to determine the number of sequences in a database that might serve as suitable sequences that can be used for referencing. In any case, any sequence that minimizes the minimum value could serve as a reference to compress, whether or not this sequence is an entry in the database. In addition, using databases with a million deep entries, depending on homology, multiple reference sequences may be used in programming for optimized organization of the dataset. As the data from the source database is streamed into a processing module, sequences may be aligned using a content addressable memory approach in the high speed data plane. This search and align routine may be useful for pre-processing and performing delta value calculations, and can be implemented in a single clock cycle in CAM.

At stage 1103A, a source or reference sequence for compression can selected or assigned or generated based on maximum homology calculations or other calculations. This may be the same minimum difference value as a sequence of one entry in said database or a consensus of all the sequences or generated or assigned by an algorithm such as was described previously herein. Additional reference sequences may also be generated, such as in an iterative process. For example, at stage 1103B, a second biological reference sequence for the database may be generated or assigned based on a combination of the calculated difference values and biological relevance of the dataset for more suitable compression. For example, the data can first be preprocessed to determine if a certain SNP or change in RFLP (restriction enzyme fragment length polymorphism) or a set profile (variation) might be present in a large portion of the entries from said dataset. In this case the procedure may include returning to the original source sequence and making appropriate changes to accommodate variations.

At stage 1103C, yet another reference sequence for the database might be generated or assigned or selected in an application specific manner. If, for example, the source database contained tens of thousands or millions of complete human genomes, a controlled source might be selected based on the delta value within a certain region with known disease association where we can apply refined optimization techniques, while using the general purpose reference sequence for the rest of the genome. The use of more than one reference sequence for instruction-based compression processing may be dependent on how much sequence variation there is between initial reference sequence selected and the entries from the database with a high difference value. In addition, the cost of having a new reference sequence as a part of the instruction database may be a determinant of using multiple biological referencing sequences for compressing a single database.

At stage 1104, delta value determinations, along with the type of database may be used to profile the references. For example, if the database contains biomarker data from breast cancer patients only, then other genes that are expected, or predicted, or yet unknown, as well as those that are known to be associated with different forms of breast cancers in addition to BRCA1 would be present. The coding language use to program the database may seamlessly include large deletions and truncations and alternative splicing in BRCA1 (or other genes) that are known, predicted, expected or yet not known to be associated with early disease onset like massive tumors before age 30, or alternatively may be these disease symptoms are known to be associated with hormonal changes that occur after first child as well. In this case, the deletion or truncation can be applied to the selected minimum controlled sequence as an updated version for more enhanced compression. Truncations are deletions at the 3' end of the gene, or in other words a premature termination codon (PTC) in the middle of the coding sequence resulting in a protein or polypeptide product with a shortened carboxyl terminus which usually does not function normally. This information may be saved for later use at stage 1106.

At stage 1105, a specific controlled source sequence may be used based on minimum delta values generated in a dictionary from the dataset, for example, for known mutation events in BRCA1 (not limited to any one gene) correlated with known clinical and/pharmacological effects. Each mutation event within each entry that results in a phenotypic effect, as well as silent mutations that are common in several entries, can be placed in a dictionary using this approach for further compression of the sequence data. As a result, processing may take advantage of specific difference values from the references that are common to multiple entries. Examples are shown below in Table 2.

TABLE 2

Hypothetical Example of BRCA Mutations With Clinical and Pharmacological Associations

| BRCA1 Mutations | Clinical Results | Pharmacological Effects |
| --- | --- | --- |
| G to A at Position 1286 | Multiple Small Tumors | Chemical X Inhibits Tumor Growth |
| Single Base Deletion at Position 932 | Positive Mammogram Result Before Age 25 | Chemical X not Effective, Highly Toxic Chemical A Low Toxicity, Low Efficacy |
| Alternative Splice Junction in the $3^{rd}$ Intron | Highly Aggressive | Chemical A Combined with Chemical Z Is Very Effective |
| AnyFrameShift Mutation Resulting in a Stop Codon Upstream of Position 1250 | Delayed Disease Onset | Chemical B is Most Effective Treatment |
| A to C at Position 547 | Most Common in Male Patients; Mild, Slow | Chemical M Effective and Nontoxic |

At stage 1106, a correlation table may be used. At this stage clinical and/or other pertinent data may be embedded in the position:instruction:destination value. Embedding data here may provide application specific compression. For example, mutation events with specific disease association or other phenotype can be coded, embedded and compressed along with the difference values in the database. At stage 1107, compressed DNA data may be stored based on selected controlled source sequence, inverse homology value, dictionary code, and other embedded data.

In addition, dictionary processing may be used, such as described previously herein. This may be based on, for example, common addresses, sized, distances or other redundancies in instruction data. Mutation events may be used as a basis in some implementations.

Figure 12:
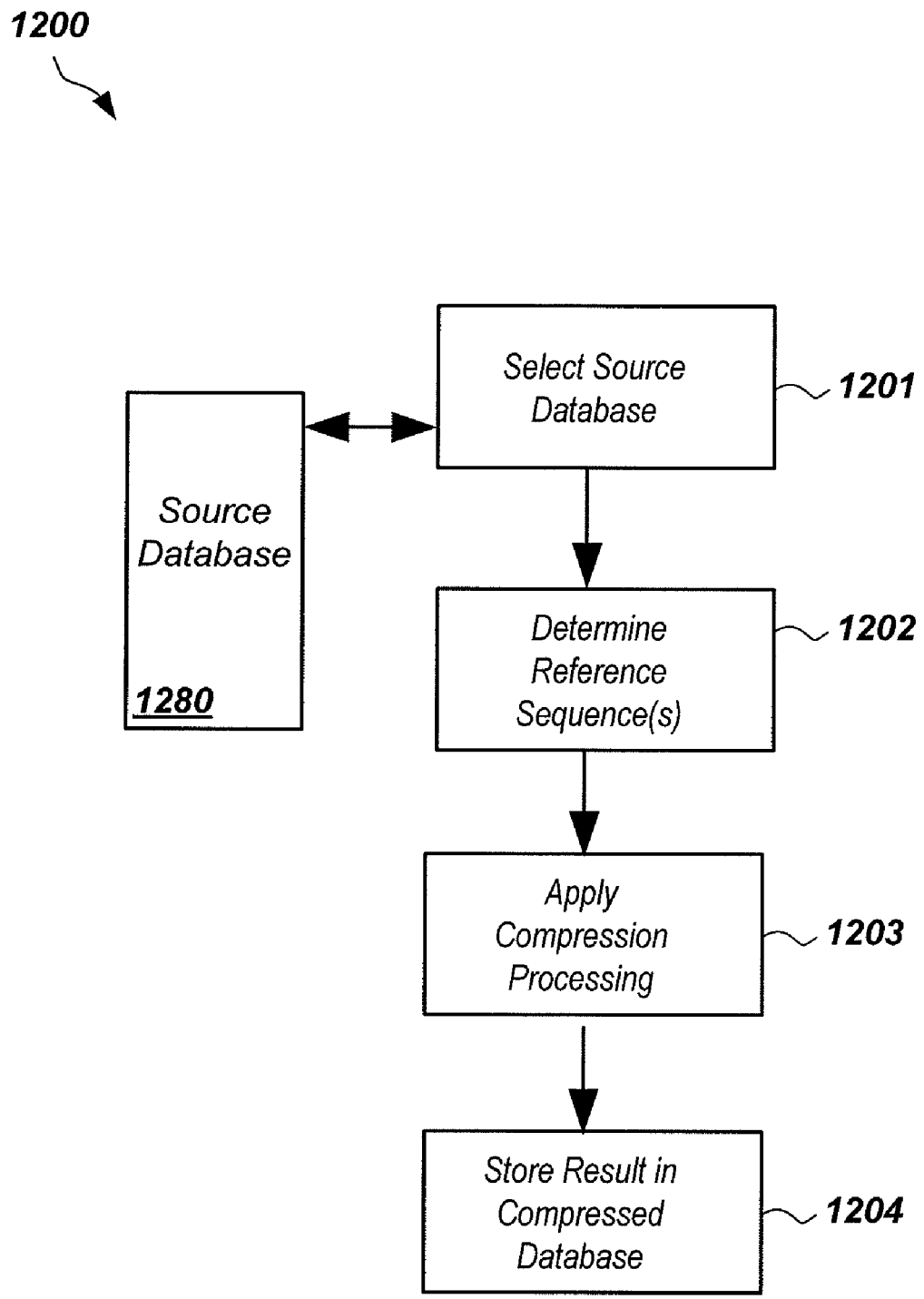
FIG. 12 illustrates an embodiment of a process for compressing of biological sequences.

Attention is now directed to FIG. 12, which illustrates details of one embodiment of a process 1200 in accordance with aspects of the present invention. At stage 1201, a database of DNA sequence data may be obtained or accessed. As an example, a large DNA sequence database may contain data from canine cancers, horse breeder data, or other animal sources. The method is not limited to any certain type of DNA data, however, the approach may be particularly effective for large database of a single species or high homology sequences. The source database may be accessed, with the data screened to meet the criteria for similarity. This preprocessing may include matching and aligning sequences in the source database. In addition, calculations for difference values and tracking of position and actions may be carried out here.

At stage 1202, a minimum reference sequence determination may be made using the delta value and other related data. At stage 1203, instruction-based compression processing, such as described previously herein, may be applied. The compression processing may take the standard DNA sequence data and converts it to a language format that is useable by a chip or other processing mechanism, which may be based on an instruction set as described previously. At stage 1204, the data stored in the compressed form retains all the information form the original sequence, and may also include other information, such as metadata. In some embodiments, this compressed format may be visible or usable only by a processing chip and/or other processing hardware, and may not be made readily available to a user.

In various embodiments, aspects of the present invention may be implemented on a computer system or systems, or may be implemented in specific semiconductor devices such as chips or chipsets or on other devices such as ASICS, programmable devices such as FPGA, or in other configurations.

Attention is now directed to FIG. 13, which illustrates one example embodiment of a computer system 1300 configured to perform biological sequence processing as described herein. System 1300 includes one or more processors 1310, along with a memory space 1370, which may include one or more physical memory devices, and may include peripherals such as a display 1320, user input output, such as mice, keyboards, etc (not shown), one or more media drives 1330, as well as other devices used in conjunction with computer systems (not shown for purposes of clarity).

System 1300 may further include a CAM memory device 1350, which is configured for very high speed data location by accessing content in the memory rather than addresses as is done in traditional memories. In addition, one or more database 1360 may be included to store data such as compressed or uncompressed biological sequences, dictionary information, metadata, or other data or information, such as computer files. Database 1360 may be implemented in whole or in part in CAM memory 1350 or may be in one or more separate physical memory devices.

System 1300 may also include one or more network connections 1340 configured to send or receive biological data, sequences, instruction sets, or other data or information from other databases or computer systems. The network connection 1340 may allow users to receive uncompressed or compressed biological sequences from others as well as send uncompressed or compressed sequences. Network connection 1340 may include wired or wireless networks, such as Etherlan networks, T1 networks, 802.11 or 802.15 networks, cellular, LTE or other wireless networks, or other networking technologies are are known or developed in the art.

Memory space 1370 may be configured to store data as well as instructions for execution on processor(s) 1310 to implement the methods described herein. In particular, memory space 1370 may include a set of biological sequence processing modules including modules for performing processing functions including reference sequence generation, in module 1380, instruction generation and instruction-based sequence compression, in modules 1382 and 1390, dictionary processing, in module 1384, metadata receipt, processing, and transmission, in module 1386, data integration, in module 1388, as well as other functions in associated modules (not shown). Instruction module 1390 may be included to provide specific functionality associated with instruction selection and processing as described previously herein.

The various modules shown in system 1300 may include hardware, software, firmware or combinations of these to perform the associated functions. Further, the various modules may be combined or integrated, in whole or in part, in various implementations. In some implementations, the functionality shown in FIG. 13 may be incorporated, in whole or in part, in one or more special purpose processor chips or other integrated circuit devices.

Figure 14:
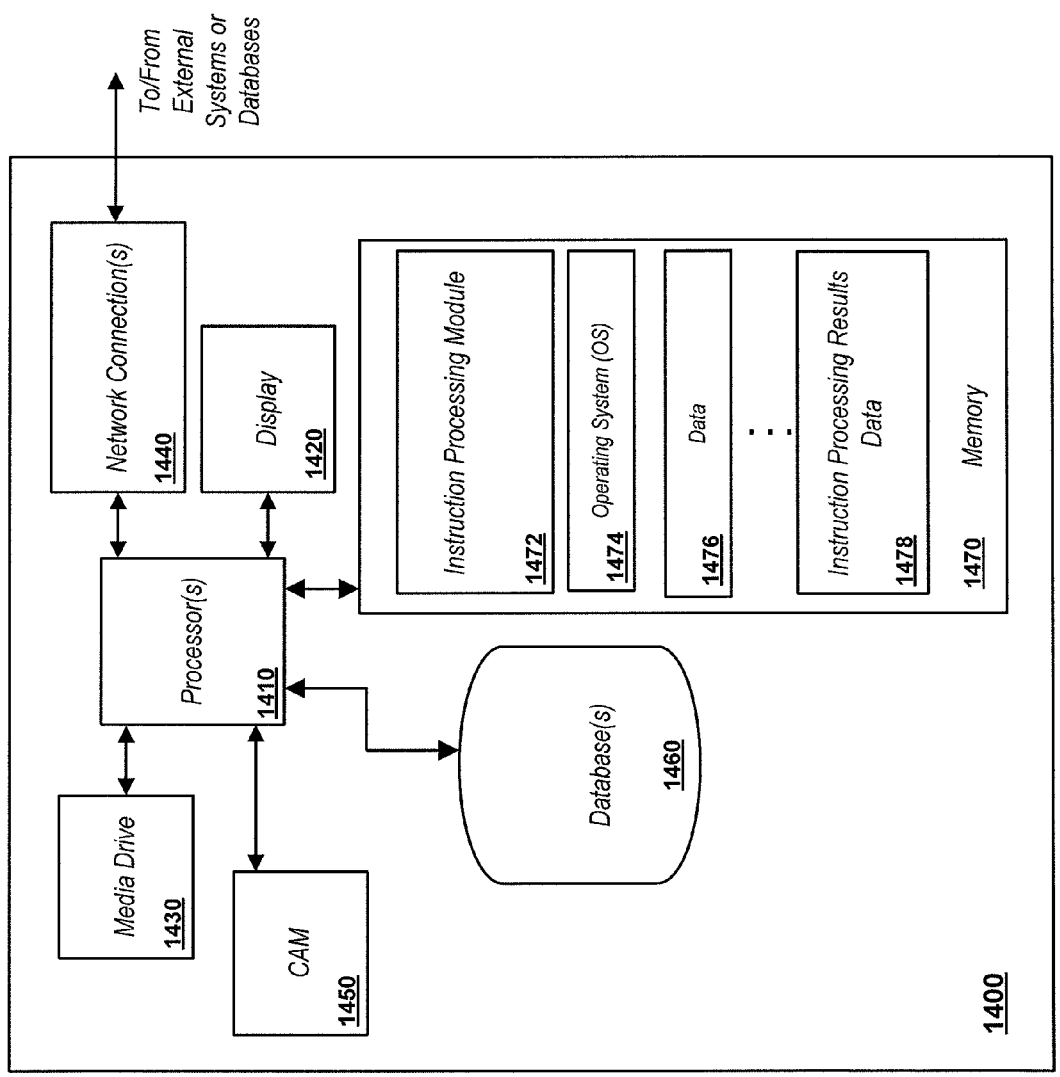
FIG. 14 illustrates an embodiment of a system for processing biological sequence data.

Attention is now directed to FIG. 14, which illustrates an example embodiment of a computer system 1400 configured to perform biological sequence processing using instructions as described herein. System 1400 may, for example, be used to implement a method for processing biopolymeric information, the method comprising receiving a sequence of binary codes representative of a biopolymeric data sequence and processing the sequence of binary codes using a plurality of instructions, each of the plurality of instructions being at least implicitly defined relative to at least one controlled sequence and representative of a biological event affecting one or more aspects of a biopolymeric molecule.

System 1400 includes one or more processors 1410, along with a memory space 1470, which may include one or more physical memory devices, and may include peripherals such as a display 1420, user input output, such as mice, keyboards, etc (not shown), one or more media drives 1430, as well as other devices used in conjunction with computer systems (not shown for purposes of clarity).

System 1400 may further include a CAM memory device 1450, which is configured for very high speed data location by accessing content in the memory rather than addresses as is done in traditional memories. In addition, one or more database 1460 may be included to store data such as compressed or uncompressed biological sequences, dictionary information, metadata or other data or information, such as computer files. Database 1460 may be implemented in whole or in part in CAM memory 1450 or may be in one or more separate physical memory devices.

System 1400 may also include one or more network connections 1440 configured to send or receive biological data, sequences, instruction sets, or other data or information from other databases or computer systems. The network connection 1340 may allow users to receive uncompressed or compressed biological sequences from others as well as send uncompressed or compressed sequences. Network connection 1340 may include wired or wireless networks, such as Etherlan networks, T1 networks, 802.11 or 802.15 networks, cellular, LTE or other wireless networks, or other networking technologies are are known or developed in the art.

Memory space 1470 may be configured to store data as well as instructions for execution on processor(s) 1410 to implement the methods described herein. In particular, memory space 1470 may include a set of biological sequence processing modules including modules for performing instruction-based processing functions as described herein. Instruction module 1490 may be included to provide specific functionality associated with instruction selection and processing including receiving a set of data including instruction set coding and providing information associated with the instruction set codes. The information may be based on comparing the instruction-set encoded information with other instruction-set encoded information or non-encoded sequence data or other data or information. The various modules shown in system 1400 may include hardware, software, firmware or combinations of these to perform the associated functions. Further, the various modules may be combined or integrated, in whole or in part, in various implementations. In some implementations, the functionality shown in FIG. 14 may be incorporated, in whole or in part, in one or more special purpose processor chips or other integrated circuit devices.

Additional Details of Embodiments of DNA Sequence Compression Architectures

In one implementation, compressed biological sequences include embedded metadata along with mutation events that are compressed with the sequence. In one embodiment, a method for compression includes a step where DNA sequence data is acquired from a source database in a standard format, such as the FASTA format, and is converted to a binary format and coded using biological instructions.

This approach may allow for streaming of the DNA data as it is converted from the standard format to a binary format. As the data streams in, the entries may be aligned and searched and processed in a CAM using the following approach. Initially, a source database may be selected where the entries are from the same species or have high sequence homology. Initially one entry from the source database or elsewhere may be selected. In other implementations, the reference sequence may be adjusted or additional reference sequences added after a dictionary analysis stage.

Once a reference sequence or sequences is selected, instruction-based compression may be applied as described herein against sequences in the source database. Based on results from initial compression processing, which may include difference values and the commonality of deltas among individual entries, a dictionary algorithm may be applied to further compress the database and also to determine if further compression may be achieved by updating or replacing the minimum controlled sequence. Finally, monitor the count of reference to dictionary entries may be monitored to determine if the reference sequence(s) should be updated. This may be done in an iterative fashion of reference sequence refinement that may be used to optimize the degree of compression.

Various embodiments may include one or more of the below described features, which may be inter-combined in various ways. Typical embodiments include machine language-like instruction with opcodes associated directly with biological sequences for the purpose of, but not limited to processing, transporting and classifying of biological sequences. A machine language is defined by, but not limited to, a set of instruction set (i.e. ISA—Instruction Set Architecture) that defines a part of the computer architecture related to programming. This may be defined for a specialized processor configured to optimally process biological instructions as described herein. The instruction set may include of group instructions including, but not limited to, biological relevance instructions of operations performed directly or indirectly on to the biological sequences in addition to, but not limited to native, operative and constructive data types, registers and its manipulations instructions, various addressing modes instructions including but not limited to absolute mode (i.e., direct, indexed, base plus indexed etc.), simple mode (i.e. register based, based plus offset, immediate, implicit and PC-relative), register indirect and sequential mode, interrupt and exception handling instructions and external I/O instructions. Macro instructions that consist of combinations of two or more instructions as described above to perform additional processing of biological sequences may also be used. Macro instructions may be used to create high level languages similar but not limited to C, C++ languages as well as object and service oriented languages tailored to processing of biological sequences Embodiments may include a micro-instruction set that is specifically designed for, but not limited to, semiconductor chip architecture including System-on Chip (SoC). Microinstructions (and/or microcode) are a set of instruction code layered between machine language code and application specific architecture of the chip. These instructions may allow to manipulation of biological sequences to provide optimal processing power based on internal chip architecture that typically includes, but is not limited to, memory architecture, register architecture, I/O and other hard coded algorithmic processing elements.

Some embodiments may use multiple optimized reference sequences to derive a difference value to be used to store a plurality of related sequences as a delta of the reference. This may include combining minimum sequence and delta values with a second set of data containing clinical, pharmacological and/or disease association data. Difference values and biological programming instruction values may be stored as a source catalog to be used for processing/parsing/sorting and compression of sequence data. Reference sequences may be updated based on iterative refinement and optimization of reference sequences using biological instructions based on mutation events that are common or otherwise related to a large portion of entries in a source database. Some embodiments may use application specific instructional programming for sequence compression and processing based in biology for known, unknown and predicted mutation and disease association.

Some embodiments may relate to programming of DNA sequence data based in biological instructions and any delta value in addition to nucleotide based on differences between entries and minimum sequences such as but not limited to, for example, base modifications (i.e. methylation, carboxylation, formylation, deamination, base analogs, etc) or structural deltas (i.e. DNA packaging; chromatin structure, heterochromatin structure, etc) or charge of partial dipolar moment or any other way to measure the difference and or homology between two entries. A programming DNA language may address mutational events in nucleic acid sequences (DNA and RNA) and amino acid sequences in protein and other polymeric molecules. Programming instructional coding may be used to address chromosomal rearrangement such as but not limited to large deletions, insertions, gene duplications, inversions and any other such related type of translocation events. Instructional operations may be used to articulate changes between and or within nucleic acid sequences including but not limited to triplet expansions in disease associations.

A biological instruction coding architecture and instruction set may be used to articulate changes between and or within nucleic acid sequences included but not limited to alternative or constitutive splicing and any known, unknown or predicted alteration in any cis-acting and or trans-acting nucleic acid or protein sequence element in disease association. Biological instruction coding may be used to articulate changes between and/or within and among nucleic acid sequences, including, but not limited to, alternative or constitutive splicing and any known, unknown, yet to be determined, or predicted alteration in any cis-acting and/or trans-acting nucleic acid or protein sequence element in gene activation, exon expression, inclusion or skipping and or disease association.

Some embodiments may include a nucleic acid programming language that can be utilized for determination of insertion element origins as related to sequences such as extraneous bacterial and or viral sequences and other such transposable elements relates to gene expression and regulation. The programming language may be configured to discriminate nucleic acid sequence insertions between DNA from microbial agents from disease causing or non disease causing origins and rearranged or shuffled genomic sequences. Some embodiments may include a biological instruction set that can enable a comparative description between two functionally or structurally related or unrelated sequences. Biological instructions may be used to operate on nucleic acid sequence data that can be used as a source of comparative analysis of sequences that are related and similar or unrelated and share little or no similarity. A programming language may use a set of instructions such as described herein, but not limited to those described herein, and to include a biological, structural, chemical or any other type of relevant or irrelevant nucleic acid sequence element for purposes of comparison, alignment, assemble, analysis, or any other related or unrelated sequence analysis and or processing. An instructional programming language may be used with any sequential element whether biologically relevant or arbitrary sequence elements used for processing and/or analysis of related or unrelated sequences.

The word "exemplary" is used herein to mean "serving as an example, instance, or illustration." Any embodiment described herein as "exemplary" is not necessarily to be construed as preferred or advantageous over other embodiments.

In some configurations, systems and apparatus for sequence compression include means for performing various functions as described herein. In one aspect, the aforementioned means may be a processor or processors and associated memory in which embodiments reside, such as is shown in system 1300 of FIG. 13, and which are configured to perform the functions recited by the aforementioned means. The may be, for example, modules or apparatus residing in system 1300 and stored in memory space 1370. In another aspect, the aforementioned means may be a module or any apparatus configured to perform the functions recited by the aforementioned means. In another aspect, the aforementioned means may be one or more integrated circuits configured to perform the functions recited by the aforementioned means. In various implementations, the means may be configured to implement the various functions, methods, processes and/or aspects as described herein, as well as others within the scope of the invention.

In one or more exemplary embodiments, the functions, methods, processes and/or aspects described herein may be implemented in hardware, software, firmware, or any combination thereof. If implemented in software, they may be stored on or encoded as one or more instructions or code on a computer-readable medium. The computer-readable medium may be part of a computer program product and may contain instructions for causing a computer to perform the methods, processes, functions and/or aspects described herein. Computer-readable media includes computer storage media. Storage media may be any available media that can be accessed by a computer or processor system. By way of example, and not limitation, such computer-readable media can comprise RAM, DRAM, SRAM, PCM, ROM, EEPROM, CD-ROM or other optical disk storage, magnetic disk storage or other magnetic storage devices, or any other medium that can be used to carry or store desired program code in the form of instructions or data structures and that can be accessed by a computer, processor or other programmable instruction-based apparatus. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

It is understood that the specific order or hierarchy of steps or stages in the processes and methods disclosed are examples of exemplary approaches. Based upon design preferences, it is understood that the specific order or hierarchy of steps in the processes may be rearranged while remaining within the scope of the present disclosure. The accompanying method claims present elements of the various steps in a sample order, and are not meant to be limited to the specific order or hierarchy presented.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps or stages of a method, process or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC or other semiconductor device. The ASIC may reside in a user terminal or other user system. In the alternative, the processor and the storage medium may reside as discrete components.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c.

The previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present invention is not intended to be limited to the embodiments shown herein but is to be accorded the widest scope consistent with the principles and novel features disclosed herein. It is intended that the following claims and their equivalents define the scope of the invention.

We claim:

1. An article of manufacture in a system for efficiently representing biopolymeric information, the article of manufacture comprising:
a non-transitory machine readable medium containing a plurality of codes executable by a processor for causing the processor to:
receive a nucleotide sequence associated with a biopolymeric molecule;
determine differences between the nucleotide sequence and a controlled biopolymeric sequence wherein the differences correspond to biological events affecting one or more aspects of the biopolymeric molecule;
generate, based upon the differences and using a defined instruction set, an instruction-encoded sequence of encoded instructions corresponding to a compressed representation of the nucleotide sequence wherein ones of the encoded instructions each include an opcode representative of a different one of the biological events and an operand relating to at least a portion of a monomer sequence of the biopolymeric molecule; and
store the instruction-encoded sequence on a machine readable memory, wherein the instruction-encoded sequence is used for biological or genetic research or for medical purposes.

2. The article of manufacture of claim 1, wherein a position of at least one of the encoded instructions within the instruction-encoded sequence relates to a location within the nucleotide sequence.

3. The article of manufacture of claim 2, wherein the biopolymeric molecule comprises a DNA molecule and wherein the monomer sequence comprises at least a portion of a nucleotide base sequence of the DNA molecule.

4. The article of manufacture of claim 3, wherein the one of the biological events comprises a transition and the operand comprises at least a first nucleotide base.

5. The article of manufacture of claim 4, wherein the operand further comprises a second nucleotide base corresponding to a result of a transition of the first nucleotide base.

6. The article of manufacture of claim 3, wherein the one of the biological events comprises a deletion.

7. The article of manufacture of claim 3, wherein the one of the biological events comprises a transversion and the operand comprises at least a first nucleotide base.

8. The article of manufacture of claim 7, wherein the operand further comprises a second nucleotide base corresponding to a result of a transversion of the first nucleotide base.

9. The article of manufacture of claim 3, wherein the one of the biological events comprises a silent mutation and the operand comprises a first nucleotide base and a second nucleotide base.

10. The article of manufacture of claim 3, wherein the one of the biological events comprises a mis-sense mutation and the operand comprises at least a first nucleotide base.

11. The article of manufacture of claim 10, wherein the operand further comprises a second nucleotide base corresponding to a result of a mis-sense mutation of the first nucleotide base.

12. The article of manufacture of claim 3, wherein the one of the biological events comprises a non-sense mutation and the operand comprises at least a first nucleotide base.

13. The article of manufacture of claim 12, wherein the operand further comprises a second nucleotide base corresponding to a result of a non-sense mutation of the first nucleotide base.

14. The article of manufacture of claim 3, wherein the one of the biological events comprises an excision and the operand comprises a sequence length.

15. The article of manufacture of claim 3, wherein the one of the biological events comprises a cross-over and the operand comprises at least a sequence length.

16. The article of manufacture of claim 3, wherein the one of the biological events represented by a first of the plurality of instructions comprises a transition and the biological event represented by a second of the plurality of instructions comprises a transversion.

17. The article of manufacture of claim 16, wherein the biological event represented by a third of the plurality of instructions comprises a mis-sense mutation and the biological event represented by a fourth of the plurality of instructions comprises a non-sense mutation.

18. The article of manufacture of claim 17, wherein the biological event represented by a fifth of the plurality of instructions comprises a silent mutation and the biological event represented by a sixth of the plurality of instructions comprises an excision.

19. The article of manufacture of claim 3, wherein one or more of the plurality of instructions are used to create a delta representation of the nucleotide base sequence relative to the controlled biopolymeric sequence.

20. The article of manufacture of claim 19, wherein the delta representation is based at least in part upon modifications of nucleotide bases in the nucleotide base sequence relative to nucleotide bases of the controlled biopolymeric sequence.

21. The article of manufacture of claim 20, wherein the modifications include one of methylation, carboxylation, and formylation.

22. The article of manufacture of claim 20, wherein the modifications include a deamination.

23. The article of manufacture of claim 19, wherein the delta representation is based at least in part upon one or more structural differences between the DNA molecule and a controlled molecular structure.

24. The article of manufacture of claim 23, wherein the one or more structural differences relate to DNA packaging.

25. The article of manufacture of claim 23, wherein the one or more structural differences relate to chromatin structure.

26. The article of manufacture of claim 23, wherein the one or more structural differences relate to heterochromatin structure.

27. The article of manufacture of claim 1, wherein the one or more aspects include a monomer sequence of the biopolymeric molecule.

28. The article of manufacture of claim 1, wherein the one or more aspects include a structure of the biopolymeric molecule.

29. The article of manufacture of claim 1, wherein the biopolymeric molecule comprises an mRNA molecule.

30. The article of manufacture of claim 29, wherein the one of the biological events represented by one of the plurality of instructions comprises a splice and the operand identifies at least one intron or exon.

31. An apparatus for processing biopolymeric information, the apparatus comprising:
   a program memory for storing a plurality of machine-executable codes; and
   a processing engine configured to execute the machine-executable codes, the processing engine;
   receiving a nucleotide sequence associated with a biopolymeric molecule:
   determining differences between the nucleotide sequence and a controlled biopolymeric sequence wherein the differences correspond to ones of a plurality of biological events affecting aspects of the biopolymeric molecule;
   generating, based upon the differences and using a defined instruction set, an instruction-encoded sequence of encoded instructions corresponding to a compressed representation of the nucleotide sequence wherein ones of the encoded instructions each include an opcode representative of a different one of the plurality of biological events and an operand relating to at least a portion of a monomer sequence of the biopolymeric molecule; and
   storing the instruction-encoded sequence on a machine readable memory, wherein the instruction-encoded sequence is used for biological or genetic research or for medical purposes.

32. The apparatus of claim 31, wherein
a position of at least one of the encoded instructions within the instruction-encoded sequence relates to a location within the nucleotide sequence.

33. The apparatus of claim 32, wherein the one of the plurality of biological events comprises a transition and the operand comprises at least a first nucleotide base.

34. The apparatus of claim 33, wherein the operand further comprises a second nucleotide base corresponding to a result of a transition of the first nucleotide base.

35. The apparatus of claim 32, wherein the one of the plurality of biological events comprises a deletion.

36. The apparatus of claim 32, wherein the one of the plurality of biological events comprises a transversion and the operand comprises at least a first nucleotide base.

37. The apparatus of claim 36, wherein the operand further comprises a second nucleotide base corresponding to a result of a transversion of the first nucleotide base.

38. The apparatus of claim 24, wherein the one of the plurality of biological events comprises a silent mutation and the operand comprises a first nucleotide base and a second nucleotide base.

39. The apparatus of claim 32, wherein the one of the plurality of biological events comprises a mis-sense mutation and the operand comprises at least a first nucleotide base.

40. The apparatus of claim 39, wherein the operand further comprises a second nucleotide base corresponding to a result of a mis-sense mutation of the first nucleotide base.

41. The apparatus of claim 32, wherein one of the plurality of biological events comprises a non-sense mutation and the operand comprises at least a first nucleotide base.

42. The apparatus of claim 41, wherein the operand further comprises a second nucleotide base corresponding to a result of a non-sense mutation of the first nucleotide base.

43. The apparatus of claim 32, wherein the one of the plurality of biological events comprises an excision and the operand comprises sequence length.

44. The apparatus of claim 32, wherein the one of the plurality of biological events comprises a cross-over and the operand comprises at least a sequence length.

45. The apparatus of claim 31, wherein the aspects include a monomer sequence of the biopolymeric molecule and a structure of the biopolymeric molecule.

46. The apparatus of claim 31, wherein the biolpolymeric molecule comprises a DNA molecule.

47. The apparatus of claim 46, wherein the biological event represented by a first of the plurality of instructions comprises a transition and the biological event represented by a second of the plurality of instructions comprises a transversion.

48. The apparatus of claim 47, wherein the biological event represented by a third of the plurality of instructions comprises a mis-sense mutation and the biological event represented by a fourth of the plurality of instructions comprises a non-sense mutation.

49. The apparatus of claim 48, wherein the biological event represented by a fifth of the plurality of instructions comprises a silent mutation and the biological event represented by a sixth of the plurality of instructions comprises an excision.

50. The apparatus of claim 46, wherein one or more of the plurality of instructions are used to create a delta representation of a nucleotide base sequence of the DNA molecule relative to the controlled biopolymeric sequence.

51. The apparatus of claim 50, wherein the delta representation is based at least in part upon modifications of nucleotide bases in the nucleotide base sequence relative to nucleotide bases of the controlled biopolymeric sequence.

52. The apparatus of claim 51, wherein the modifications include one of methylation, carboxylation, and formylation.

53. The apparatus of claim 5, wherein the modifications include deamination and base analog.

54. The apparatus of claim 50, wherein the delta representation is based at least in part upon one or more structural differences between the DNA molecule and a controlled molecular structure.

55. The apparatus of claim 54, wherein the one or more structural differences relate to DNA packaging.

56. The apparatus of claim 54, wherein the one or more structural differences relate to chromatin structure.

57. The apparatus of claim 54, wherein the one or more structural differences relate to a heterochromatin structure.

58. The apparatus of claim 31, wherein the biopolymeric molecule comprises an mRNA molecule.

59. The apparatus of claim 58, wherein the biological event represented by one of the plurality of instructions comprises a splice and the operand comprises at least one intron or exon.

60. A computer program product comprising a non-transitory computer readable medium including codes for causing a computer to:
receive a sequence of binary codes representative of a biopolymeric data sequence;
generate, by processing the sequence of binary codes using a plurality of instructions, an instruction-encoded sequence of encoded instructions corresponding to a compressed representation of the biopolymeric data sequence, each of the encoded instructions being representative of one of a plurality of biological events affecting one or more aspects of a biopolymeric molecule;
wherein ones of the encoded instructions each include an opcode representative of one of the plurality of biological events and an operand relating to at least a portion of a monomer sequence of the biopolymeric molecule; and
store the instruction-encoded sequence on a machine readable memory, wherein the instruction-encoded sequence is used for biological or genetic research or for medical purposes.

61. The computer program product of claim 60, wherein the codes further include codes for:
defining one or more macro instructions comprised of two or more instructions of the plurality of instructions; and
processing the sequence of binary codes using the one or more macro instructions.

62. The computer program product of claim 60, wherein the codes include codes for deriving a delta representation of the biopolymeric data sequence using a reference sequence.

63. The computer program product of claim 62, wherein the biopolymeric data sequence comprises a DNA sequence.

64. The computer program product of claim 63, wherein the delta representation is based at least upon differences between a nucleotide base sequence of the biopolymeric data sequence and a reference nucleotide base sequence of the reference sequence.

65. The computer program product of claim 64, wherein the delta representation is further based upon modifications of nucleotide bases in the nucleotide base sequence of the biopolymeric data sequence relative to nucleotide bases in the reference base sequence.

66. The computer program product of claim 60, wherein one or more of the plurality of instructions are used to represent a mutation in the biopolymeric data sequence.

67. A computer program product comprising a non-transitory computer readable medium including codes for causing a computer to:
receive a sequence of binary codes representative of a biopolymeric data sequence;
process the sequence of binary codes using a plurality of instructions in order to yield an instruction-encoded sequence of encoded instructions corresponding to a compressed representation of the biopolymeric data sequence, each of the plurality of instructions being representative of a biological event affecting one or more aspects of a biopolymeric molecule;
wherein ones of the encoded instructions each include an opcode representative of one of the plurality of biological events and an operand relating to at least a portion of a monomer sequence of the biopolymeric molecule; and
store the instruction-encoded sequence on a machine readable memory, wherein the instruction-encoded sequence is used for biological or genetic research or for medical purposes.

* * * * *